(12) United States Patent
Chang et al.

(10) Patent No.: US 11,950,491 B2
(45) Date of Patent: Apr. 2, 2024

(54) SEMICONDUCTOR MIXED MATERIAL AND APPLICATION THEREOF

(71) Applicant: Raynergy Tek Incorporation, Hsinchu (TW)

(72) Inventors: Yi-Ming Chang, Hsinchu (TW); Chuang-Yi Liao, Hsinchu (TW); Wei-Long Li, Hsinchu (TW); Yu-Tang Hsiao, Hsinchu (TW); Chun-Chieh Lee, Hsinchu (TW); Chia-Hua Li, Hsinchu (TW); Huei-Shuan Tan, Hsinchu (TW)

(73) Assignee: RAYNERGY TEK INCORPORATION, Hsinchu (TW)

( * ) Notice: Subject to any disclaimer, the term of this patent is extended or adjusted under 35 U.S.C. 154(b) by 72 days.

(21) Appl. No.: 16/950,600

(22) Filed: Nov. 17, 2020

(65) Prior Publication Data
US 2021/0336148 A1    Oct. 28, 2021

(30) Foreign Application Priority Data

Apr. 28, 2020   (TW) .................... 109114201

(51) Int. Cl.
*H10K 85/10*   (2023.01)
*C07D 495/22*   (2006.01)
(Continued)

(52) U.S. Cl.
CPC ......... *H10K 85/113* (2023.02); *C07D 495/22* (2013.01); *C08G 61/126* (2013.01);
(Continued)

(58) Field of Classification Search
CPC ............. H01L 51/0036; H01L 51/0043; H01L 51/0047; H01L 51/0053; H01L 51/0058;
(Continued)

(56) References Cited

U.S. PATENT DOCUMENTS

| | | | |
|---|---|---|---|
| 2014/0174536 A1 | 6/2014 | Gong | |
| 2017/0288156 A1 | 10/2017 | Son | |

(Continued)

FOREIGN PATENT DOCUMENTS

| | | | |
|---|---|---|---|
| CN | 103262277 A | 8/2013 | |
| TW | 201141902 A | 12/2011 | |

(Continued)

OTHER PUBLICATIONS

Ming-Ao Pan "16.7%-efficiency ternary blended organic photovoltaic cells with PCBM as the acceptor additive to increase the open-circuit voltage and phase purity" J. Mater. Chem. A, 2019, 7, 20713 (Year: 2019).*

(Continued)

*Primary Examiner* — Michael Y Sun
(74) *Attorney, Agent, or Firm* — WPAT, P.C.

(57) ABSTRACT

A semiconductor mixed material comprises an electron donor, a first electron acceptor and a second electron acceptor. The first electron donor is a conjugated polymer. The energy gap of the first electron acceptor is less than 1.4 eV. At least one of the molecular stackability, $\pi$-$\pi$*stackability, and crystallinity of the second electron acceptor is smaller than the first electron acceptor. The electron donor system is configured to be a matrix to blend the first electron acceptor and the second electron acceptor. The present invention also provides an organic electronic device including the semiconductor mixed material.

8 Claims, 8 Drawing Sheets

(51) Int. Cl.
*C08G 61/12* (2006.01)
*C08K 3/04* (2006.01)
*C08K 5/45* (2006.01)
*C08K 5/46* (2006.01)
*C08K 13/06* (2006.01)
*H10K 85/20* (2023.01)
*H10K 85/60* (2023.01)
*H10K 30/30* (2023.01)

(52) U.S. Cl.
CPC ............ *C08K 3/045* (2017.05); *C08K 5/45* (2013.01); *C08K 5/46* (2013.01); *C08K 13/06* (2013.01); *H10K 85/151* (2023.02); *H10K 85/215* (2023.02); *H10K 85/621* (2023.02); *H10K 85/626* (2023.02); *H10K 85/655* (2023.02); *H10K 85/6576* (2023.02); *C08G 2261/122* (2013.01); *C08G 2261/124* (2013.01); *C08G 2261/1412* (2013.01); *C08G 2261/1424* (2013.01); *C08G 2261/3223* (2013.01); *C08G 2261/3246* (2013.01); *C08G 2261/3247* (2013.01); *C08G 2261/514* (2013.01); *C08K 2201/001* (2013.01); *C08K 2201/011* (2013.01); *H10K 30/30* (2023.02)

(58) Field of Classification Search
CPC .............. H01L 51/0068; H01L 51/0074; H01L 51/4253; H01L 51/0003; H01L 51/0035; H01L 51/0094; C07D 495/22; C08G 61/126; C08G 2261/122; C08G 2261/124; C08G 2261/1412; C08G 2261/1424; C08G 2261/3223; C08G 2261/3246; C08G 2261/3247; C08G 2261/514; C08G 2261/146; C08G 2261/164; C08G 2261/1642; C08G 2261/1646; C08G 2261/3142; C08G 2261/316; C08G 2261/3243; C08G 2261/51; C08G 2261/90; C08K 3/045; C08K 5/45; C08K 5/46; C08K 13/06; C08K 2201/001; C08K 2201/011
See application file for complete search history.

(56) References Cited

U.S. PATENT DOCUMENTS

2019/0013474 A1   1/2019  Yan
2021/0119130 A1*  4/2021  Yan .................... H01L 51/0046

FOREIGN PATENT DOCUMENTS

TW   201323428 A   6/2013
TW   201509983 A   3/2015
TW   201829399 A   8/2018

OTHER PUBLICATIONS

Jun Yuan "Single-Junction Organic Solar Cell with over 15% Efficiency Using Fused-Ring Acceptor with Electron-Deficient Core" Joule 3, 1140-1151 Apr. 17, 2019 (Year: 2019).*
Jianhui Hou "Synthesis, Characterization, and Photovoltaic Properties of a Low Band Gap Polymer Based on Silole-Containing Polythiophenes and 2,1,3-Benzothiadiazole" J. Am. Chem. Soc. 2008, 130, 16144-16145 (Year: 2008).*
Tomoya Higashihara "Synthesis of New Thiadiazole-Containing Polythiophene Derivatives and Their Application to Organic Solar Cells" Journal of Photopolymer Science and Technology, vol. 26, No. 2 (2013) 185-191 (Year: 2013).*
Hu et al. "Terthiophene-Based D—A Polymer with an Asymmetric Arrangement of Alkyl Chains That Enables Efficient Polymer Solar Cells", 2015, Journal of the American Chemical Society.
Hu et al. "Influence of Donor Polymer on the Molecular Ordering of Small Molecular Acceptors in Nonfullerene Polymer Solar Cells", 2018, Advanced Energy Materials.
China Patent Office "Office Action" dated Aug. 24, 2023, China.
Taiwan Patent Office "Office Action" dated Jul. 21, 2021, Taiwan.

* cited by examiner

SEMICONDUCTOR MIXED MATERIAL AND APPLICATION THEREOF

The present application is based on, and claims priority from, Taiwan patent application No. 109114201, filed on Apr. 28, 2020, the disclosure of which is hereby incorporated by reference herein in its entirety.

BACKGROUND OF THE INVENTION

Field of the Invention

The present invention relates to a semiconductor mixed material applied to an organic photochemistry or electronic device, and an active layer including the semiconductor mixed material and an organic electronic device.

Description of the Prior Art

In view of global warming, climate change has become a common challenge in the international communities. The Kyoto protocol proposed by the "United Nations Framework Convention on Climate Change (UNFCCC)" in 1997 which had entered into force in 2005 is aimed at reducing carbon dioxide emissions. In this regard, countries are focusing on the development of renewable energy to reduce the use of petrochemical fuels. As the sun provides far enough energy needs of people at present and for the future, renewable energy becomes a major concern for solar power generation, which has led to the use of organic electric devices for solar power generation as the primary development target.

Compared with the existing silicon-based organic electric devices, the new type of organic electric devices is not only cheap in production cost and light weight, but also can be thin, transparent and flexible as plastic films, so that the new type of organic electric devices is suitable for making various shapes. The organic electric devices can be widely used in communication, architecture, transportation, lighting, fashion and other fields. Therefore, the new generation of organic electric devices not only contributes to environmental protection during global climate change, but also has great economic potential.

In the past ten years, through the design of materials and devices, the efficiency of Organic Solar Cell (OSC) has been significantly improved. However, the organic solar cell is limited by the narrow absorption characteristic of the organic material, so that the binary polymer blend films is difficult to be come true by using the characteristic of the spectral broadening of the solar energy effectively. In addition, there is always a contradiction between phase blending (benefit to the exciton dissociation) and phase separation (benefit to the charge transfer), which restricts further breakthroughs in the efficiency of organic electronic devices.

However, the active layer of the organic electronic device of the present market usually has consist of at least two materials in that. In the prior art, the mixed materials with the electron donor and the electron acceptor are difficult to reduce the problem of the leakage current generation and the weak light absorption in the near infrared area. Hence, how to develop a mixed material to solve the above problems is an important issue at present.

SUMMARY OF THE INVENTION

In view of this, one category of the present invention is to provide a semiconductor mixed material to solve the prior art problems. According to a specific embodiment of the present invention, the semiconductor mixed material comprises an electron donor, a first electron acceptor and a second electron acceptor. The electron donor is a conjugated polymer. The first electron acceptor with an energy gap is less than 1.4 eV, and the first electron acceptor comprising a structure of Formula I:

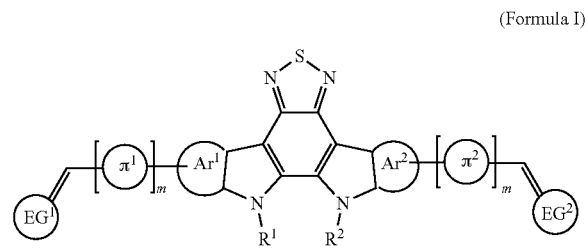

(Formula I)

wherein $R^1$ and $R^2$ can be the same or different, and $R^1$ and $R^2$ are independently selected from the group consisting of C1-C30 alkyl chain with substituents and without substitutents, and halogen; $Ar^1$, $Ar^2$, $EG^1$ and $EG^2$ can be the same or different, and $Ar^1$, $Ar^2$, $EG^1$ and $EG^2$ are independently selected from the group consisting of C1-C30 fused ring with and without substituents, C1-C30 fused heteroaromatic ring with and without substituents substituents, and C1-C30 fused heterocyclic ring with and without substituents, benzene rings with and without substituents, five-membered heterocyclic ring with and without substituents, and six-membered heterocyclic rings with and without substituents; and $\pi^1$ and $\pi^2$ can be the same as or different from each other, and $\pi^1$ and $\pi^2$ are independently selected from the group consisting of C1-C30 fused ring with and without substituents, C1-C30 fused heterocyclic ring with and without substituents, C1-C30 fused ring with and without substituents, benzene ring with and without substituents, five-membered ring with and without substituents, and six-membered ring with and without substituents, alkene and alkyne with and without substituents, wherein m is an integer selected from 0 to 5; and a second electron acceptor, wherein at least one of molecular stacking, π-π* stacking, and crystallization of the second electron acceptor is less than that of the first electron acceptor; wherein, the electron donor is configured as a substrate for mixing the first electron acceptor and the second electron acceptor.

wherein $R^1$ and $R^2$ can be the same or different from each other, and $R^1$ and $R^2$ are independently selected from the group consisting of C1-C30 alkyl chain with carbon branched chain structure with substituents and without substituents.

wherein the substituent of Formula I is one selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 alkene, C1-C30 alkyne, C1-C30 cyano-containing carbon chain, C1-C30 nitro-containing carbon chain, C1-C30 hydroxy-containing carbon chain, C1-C30 keto-containing carbon chain, oxygen, and halogen.

wherein the second acceptor comprises at least one structure of Formula II, Formula III, and Formula IV:

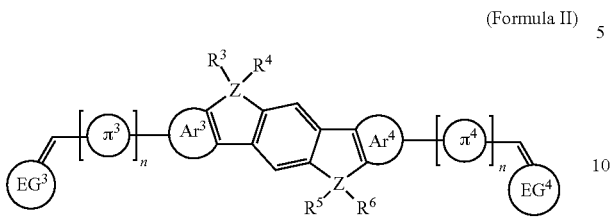
(Formula II)

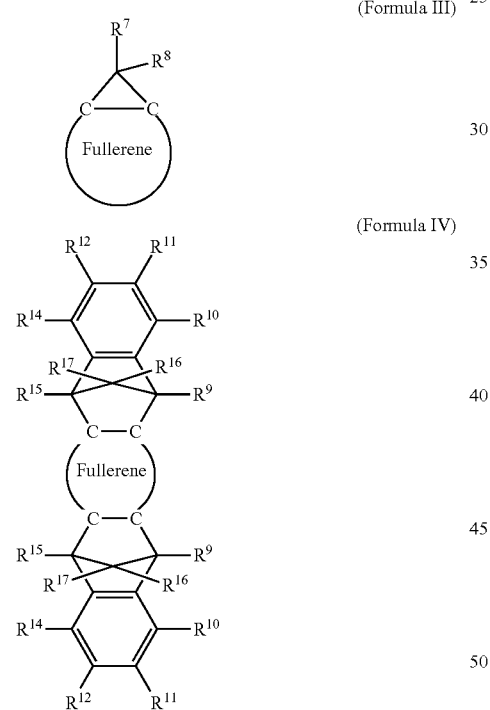

(Formula III)

(Formula IV)

wherein, Z is selected from one of following C, Si, and Ge; R3 to $R^{17}$ can be the same or different, and R3 to $R^{17}$ are independently selected from the group consisting of C1-C30 alkyl chain with substituents and without substituents and halogen; $Ar^3$, $Ar^4$, $EG^3$, $EG^4$ can be the same or different, and $Ar^3$, $Ar^4$, $EG^3$, $EG^4$ are independently selected from the group consisting of C1-C30 fused ring with and without substituents, C1-C30 fused heteroaromatic rings with and without substituents, and C1-C30 fused heterocyclic ring with and without substituents, benzene rings with and without substituents, five-membered heterocyclic ring with and without substituents, and six-membered heterocyclic ring with and without substituents; and $\pi^3$ and $\pi^4$ can be the same or different, and $\pi^3$ and $\pi^4$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents, alkene and alkyne with and without substituents, wherein m is any integer selected from 0 to 5.

wherein the electron donor further comprises the structure of Formula V:

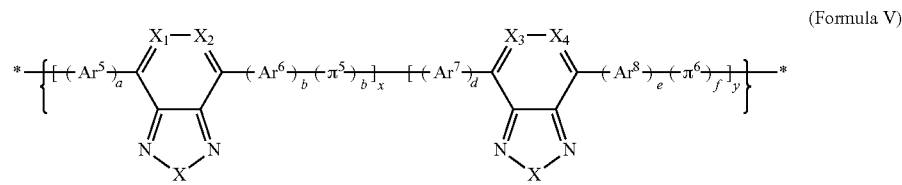
(Formula V)

wherein, X is selected from one of following C, S, N, and O; $X_1$ to $X_4$ can be the same s or different, and $X_1$ to $X_4$ are independently selected from the group consisting of C, C—F, C—Cl, C—Br, and C—I; $Ar^5$ to $Ar^8$ can be the same as or different from each other, and $Ar^5$ to $Ar^8$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents; $\pi^5$ and $\pi^6$ can be the same or different, and $\pi^5$ and $\pi^6$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, six-membered ring with and without substituents, and alkenes and alkynes with and without substituents; a to f can be the same or different, and a to f are integers independently selected from 0 to 5; and the sum of x and y is 1.

wherein one of $Ar^5$ to $A^8$ further comprises at least one of Si and S.

wherein the weight percentage of the first electron acceptor is not less than that of the second electron acceptor in the semiconductor mixed material.

According to another category of the present invention is to provide an organic semiconductor mixed material, the organic semiconductor mixed material comprising a electron donor, a first electron donor and a second electron donor. The electron donor is a conjugated polymer. The first electron acceptor with an energy gap is less than 1.4 eV. At least one of the characteristic of the molecular stackability, the π-π* stackability, the crystallinity of the second electron acceptor are less than the first electron acceptor, and the second electron donor comprising at least one of the structure of Formula II, Formula III, and Formula IV (Formula II)

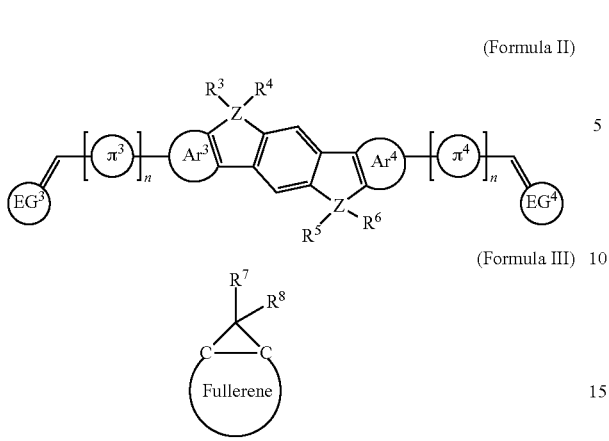

(Formula III)

-continued (Formula IV)

wherein, Z is one selected from the group consisting of C, Si, and Ge; $R^3$ to $R^{17}$ can be the same or different, and $R^3$ to $R^{17}$ are independently selected from the group consisting of C1-C30 alkyl chain with substituents and without substituents and halogen; $Ar^3$, $Ar^4$, $EG^3$, $EG^4$ can be the same or different, and $Ar^3$, $Ar^4$, $EG^3$, $EG^4$ are independently selected from the group consisting of C1-C30 fused ring with and without substituents, C1-C30 fused heteroaromatic ring with and without substituents, and C1-C30 fused heterocyclic ring with and without substituents, benzene ring with and without substituents, five-membered heterocyclic ring with and without substituents, and six-membered hetero- clic ring with and without substituents; and $\pi^3$ and $\pi^4$ can be the same or different, and $\pi^3$ and $\pi^4$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents, alkene and alkyne with and without substituents, wherein m is an integer selected from 0 to 5. wherein, the electron donor is configured as a substrate for mixing the first electron acceptor and the second electron acceptor.

wherein the electron donor further comprises a structure of Formula V:

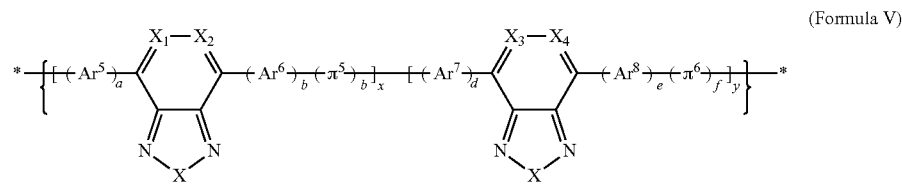

(Formula V)

wherein, X is selected from one of C, S, N, and O; $X_1$ to $X_4$ can be the same or different, and $X_1$ to $X_4$ are independently selected from the group consisting of C, C—F, C—Cl, C—Br, and C—I; $Ar^5$ to $Ar^8$ can be the same or different, and $Ar^5$ to $Ar^8$ are independently selected from the group consisting of C1-C30 fused rings with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents; $\pi^5$ and $\pi^6$ can be the same or different, and $\pi^5$ and $\pi^6$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, six-membered ring with and without substituents, and alkenes and alkynes with and without substituent; a to f can be the same or different, and a to f are integer independently selected from 0 to 5; and the sum of x and y is 1.

According to the other category of the present invention is to provide an organic electronic device, comprising a first electrode, a second electrode, and an active layer material. The active layer is located between the first electrode and the second electrode, wherein the active layer material comprises the semiconductor mixed material as described in any one of the above two categories.

Compared with the prior art, the semiconductor mixed material of the present invention can effectively improve the leakage current of the organic electronic device and external quantum efficiency (EQE).

BRIEF DESCRIPTION OF THE APPENDED DRAWINGS

Some of the embodiments will be described in detail, with reference to the following figures, wherein like designations denote like members, wherein.

Figure 1:
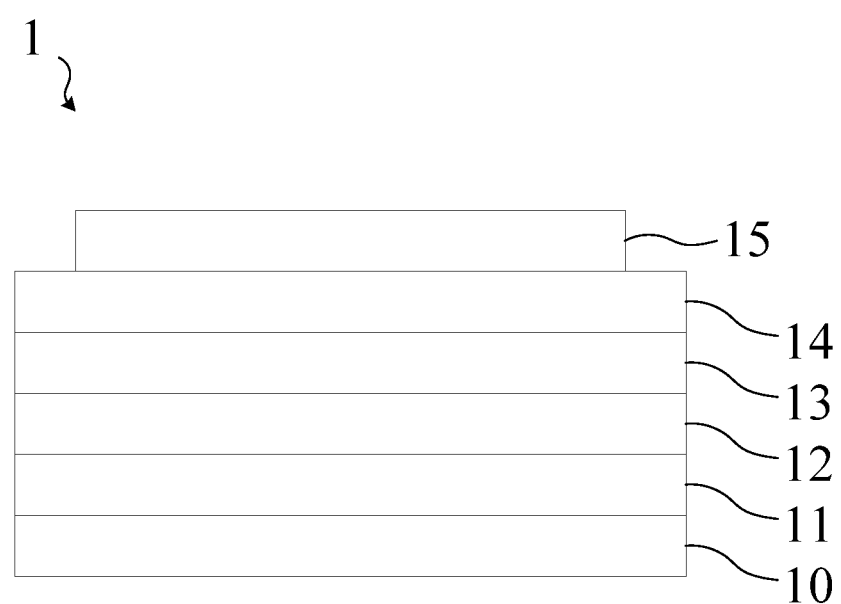
FIG. 1 shows a schematic structural diagram of one embodiment of the organic electronic device of the present invention.

The advantages, spirits, and features of the present invention will be explained and discussed with embodiments and figures as follows.

DETAILED DESCRIPTION OF THE INVENTION

In order to make the advantages, spirit and features of the present invention easier and clearer, it will be detailed and discussed in the following with reference to the embodiments and the accompanying drawings. It is worth noting that the specific embodiments are merely representatives of the embodiments of the present invention, but it can be implemented in many different forms and is not limited to the embodiments described in this specification. Rather, these embodiments are provided so that this disclosure will be thorough and complete.

The terminology used in the various embodiments disclosed in the present invention is only for the purpose of describing specific embodiments, and is not intended to limit the various embodiments disclosed in the present invention. As used herein, singular forms also include plural forms unless the context clearly indicates otherwise. Unless otherwise defined, all terms (including technical and scientific terms) used in this specification have the same meanings as commonly understood by one of ordinary skill in the art to which the various embodiments disclosed herein belong. The above terms (such as those defined in commonly used dictionaries) will be interpreted as having the same meaning as the contextual meaning in the same technical field, and will not be interpreted as having an idealized or overly formal meaning, unless explicitly defined in the various embodiments disclosed herein.

In the description of this specification, the description of the reference terms "an embodiment", "a specific embodiment" and the like means that specific features, structures, materials, or characteristics described in connection with the embodiment are included in at least one embodiment of the present invention. In this specification, the schematic expressions of the above terms do not necessarily refer to the same embodiment. Furthermore, the particular features, structures, materials, or characteristics described may be combined in any suitable manner in any one or more embodiments.

Definition

As used herein, "donor" material refers to a semiconductor material, such as a semiconductor material, having electron holes as a primary current or charge carrier. In some embodiments, when a p-type semiconductor material is deposited on a substrate, it can provide the electron holes with a hole mobility greater than about $10^{-5}$ cm$^2$/Vs. In the case of field effect devices, current on/off ratio of the p-type semiconductor material exhibits more than about 10.

As used herein, "acceptor" material refers to the semiconductor material, such as the semiconductor material, having electrons as the primary current or the charge carrier. In some embodiments, when a n-type semiconductor material is deposited on a substrate, it can provide the electrons with an electron mobility greater than about $10^{-5}$ cm$^2$/Vs. In the case of field effect devices, current on/off ratio of the n-type semiconductor material exhibits more than about 10.

As used herein, "mobility" refers to a speed rate of the charge carrier moving through the material under the influence of an electric field. The charge carrier is the electron hole (positive charge) in the p-type semiconductor material and the electron (negative charge) in the n-type semiconductor material. This parameter depends on architecture of device and can be measured by field effect device or space charge limiting current.

The compound as used herein is considered as "environmentally stable" or "stabilized under ambient conditions" and refers to that the carrier mobility of the transistor of the semiconductor material utilized the compound is maintained at initial value while the transistor has been exposed to an environmental condition such as air, environmental temperature and humidity for a duration. For example, a compound may be considered to be environmentally stable if the change in carrier mobility of a transistor incorporating the compound is less than 20% or 10% of the initial value after being exposed to the environmental conditions including air, humidity and temperature for 3, 5 or 10 days.

Fill factor (FF) used herein refers to the ratio of the actual maximum available power ($P_m$ or $V_{mp}*J_{mp}$) to the theoretical (non-actually available) power ($J_{sc}*V_{oc}$). Therefore, the fill factor can be determined by the following formula: FF=$(V_{mp}*J_{mp})/(V_{oc}*J_{sc})$; Wherein, the $J_{mp}$ and $V_{mp}$ respectively represent the current density and voltage at the maximum power point ($P_m$), which is obtained by varying the resistance in the circuit to the maximum value of J*V. $J_{sc}$ and $V_{oc}$ represent open circuit current and open circuit voltage, respectively. The fill factor is a key parameter for evaluating solar cells. The fill factor of commercial solar cells is typically greater than about 0.60%.

The open circuit voltage (Voc) used herein is the potential difference between the anode and the cathode of the device without connecting the external load.

The power conversion efficiency (PCE) of solar cells used herein refers to the conversion percentage of power from the incident light to the electricity power. The power conversion efficiency (PCE) of solar cells can be calculated by dividing the maximum power point ($P_m$) by the incident light irradiance (E; $W/m^2$) under the standard test conditions (STC) and the surface area (Ac; $m^2$) of the solar cells. STC generally refers to the conditions of temperature of 25° C., irradiance of 1000 W/m2, and air mass (AM) 1.5 spectrum.

The member (e.g., a thin film layer) as used herein can be considered as "photoactive" if it contains one or more compounds capable of absorbing photons to generate excitons for producing photocurrents.

As used herein, "solution proceeding" refers to a process in which a compound (e.g., a polymer), material, or composition can be used in a solution state, such as spin coating, printing (e.g., inkjet printing, gravure printing, and lithography printing), spray coating, slit coating, drop casting, dip coating, and knife coating.

As used herein, "annealing" refers to a post-deposition heat treatment to a semi-crystalline polymer film for certain duration in the environment or under decompressed or pressurized environment. "Annealing temperature" refers to the temperature at which the polymer film or the mixed film of the polymer and other molecules can perform small-scale molecular movement and rearrangement during the annealing process. Without limitation by any particular theory, it is believed that annealing can lead to an increase in crystallinity in the polymer film, enhance the material carrier mobility of the polymer film or a mixed film of the polymer with other molecules, and the molecules are arranged alternately to achieve the effect of independent transmission paths of effective electrons and holes.

As used herein, "polymer compound" (or "polymer") refers to a molecule comprising a plurality of one or more repeating units bonded by covalent bond. A polymer compound (polymer) can be represented by the following formula: *-(-(Ma)x-(Mb)y-)$_z$*; wherein each Ma and Mb is a repeating unit or a monomer. The polymer compound may comprise only one type of repeating unit, or may comprise two or more different repeating units. When the polymeric compound comprises only one type of repeating units, it may be referred to as a homopolymer. When the polymeric compound comprises two or more than two types of repeating units, it may be referred to as "copolymer" or "copolymeric compound". For example, the copolmeric compound can comprise different repeating units Ma and Mb. Unless otherwise indicated, the assembly of the repeating units in the copolymer can be head to tail, head to head or tail to tail. Further, the copolymer may be a random copolymer, an alternating copolymer or a block copolymer unless otherwise indicated. For example, the general formula (I) can be used to represent the copolymer having Ma with x molar fraction and Mb with y mole fraction, wherein the comonomers of Ma and Mb can be repeated in alternately, irregular, regional regiorandom, regional rules or blocks, and the comonomers of Ma and Mb can exist up to z comononmers. In addition to its composition, a polymeric compound, according to measurement techniques, can be described by degree of polymerization (n) or molar mass (e.g., number average molecular weight (Mn), and/or weight average molecular weight (Mw).

As used herein, "halo" or "halogen" means fluoro, chloro, bromo and iodo.

As used herein, "alkyl" refers to a straight or branched saturated hydrocarbon. For example, alkyl includes methyl (Me), ethyl (Et), propyl (e.g. n-propyl and iso-propyl), butyl (e.g. n-butyl, iso-butyl, t-butyl, and tert-butyl), pentyl (e.g. n-pentyl and iso-pentyl), hexyl, and the like. In various embodiments, the alkyl can have 1 to 40 carbon atoms (i.e., C1-40 alkyl), such as 1 to 30 carbon atoms (i.e., C1-30 alkyl). In some embodiments, the alkyl can have 1 to 6 carbon atoms and can be referred to as a "lower alkyl." For example, the lower alkyl includes methyl, ethyl, propyl (e.g., n-propyl and iso-propyl), and butyl (e.g., n-butyl, iso-butyl, t-butyl, and ten-butyl). In some embodiments, alkyl can be substituted as described herein. Generally, alkyl would not be substituted by another alkyl, alkenyl or alkynyl.

Substituted alkyl groups may, depending on the length of the alkyl chain, have one or more (e.g. 1, 2, 3, 4, 5 or more than 5) substituents. Preferably, each is independently selected from alkyl, aryl, heteroaryl, fluorine, chlorine, bromine, hydroxyl, mercapto, cyano, nitro, nitroso, formyl, naphthyl, carboxylate, alkoxycarbonyl, cycloalkylamino, alkyl, aryl and heteroaryl substituents and can be substituted or substituted. The suitable substituents such as methoxy, sulfonate, sulfamino, sulfamide, and amidino groups are the substituents mentioned above for these groups.

The above remarks regarding unsubstituted and substituted alkyl also apply to unsubstituted and substituted alkoxy.

As used herein, "alkenyl" refers to straight or branched carbon chain having one or more carbon-carbon double bonds. For example, alkenyl includes vinyl, propenyl, butenyl, pentenyl, hexenyl, butadienyl, pentadienyl, hexadienyl and the like. One or more carbon-carbon double bond may be located in internal (e.g., 2-butene) or terminal (e.g., 1-butene). In various embodiments, alkenyl can have 2 to 40 carbon atoms (i.e., C2-40 alkenyl) or 2 to 20 carbon atoms (i.e., C2-20 alkenyl). In some embodiments, alkenyl can be substituted as described herein. Generally, Alkenyl would not be substituted by another alkenyl, alkyl or alkynyl.

As used herein, "fused ring" or "fused ring group" refers to a polycyclic system having at least two rings, and at least one of which is an aromatic ring, wherein the aromatic ring (carbocyclic or heterocyclic) shares a bond with at least one aromatic or non-aromatic ring (carbocyclic or heterocyclic). The polycyclic systems can be highly it-conjugated systems as described herein, or be selectively substituted as described herein.

As used herein, "heteroatom" means an atom of any element other than carbon and hydrogen, such as nitrogen, oxygen, helium, sulfur, phosphorus, and selenium.

As used herein, "aryl" refers to an aromatic monocyclic hydrocarbon ring system, or polycyclic system which is fused by one or more aromatic hydrogen rings, or fused by at least one aromatic monocyclic hydrocarbon ring with one or more cycloalkyl rings and/or heterocyclic rings. The aryl may contain 6 to 24 carbon atoms (e.g., C6-C24 aryl) and may include a plurality of fused rings. In some embodiments, the polycyclic aromatic group can have 8 to 24 carbon atoms. Any suitable ring position in the aryl can be covalently bonded to a defined chemical structure. Examples of the aromatic groups having an aromatic carbocyclic ring include phenyl, 1-naphthyl (bicyclic), 2-naphthyl (bicyclic), fluorenyl (tricyclic), phenanthryl (tricyclic), and pentacyl (five rings) and so on. Examples of the polycyclic system in which at least one aromatic monocyclic hydrocarbon ring is fused to one or more cycloalkyl rings and/or heterocyclic rings, comprises benzene derivatives containing cyclopentane (i.e., fluorenyl, and 5,6-bicycloalkyl/aromatic ring system), benzene derivatives containing cyclohexane (i.e., tetrahydronaphthyl, and 6,6-biscycloalkane/aromatic ring system), benzene derivatives containing imidazolines (i.e., benzimidazolinyl, 5,6-bicyclic heterocyclyl/aromatic ring system), and benzene derivatives containing pyran (i.e., benzopyranyl, and 6,6-bicyclic heterocyclic/aromatic ring system). Other examples of aryl group include benzodioxanyl, benzodioxolyl, chromanyl, porphyrin, and the like. In some embodiments, aryl can be substituted as described herein. In some embodiments, aryl can have one or more halogen substituent and can also be referred to as halogen aryl. Perhaloaryl, which is included in the halogen substituent, is that all of hydrogen atoms in aryl are replaced by halogen atom (for example, $C_6F_5$). In certain embodiments, one of the substituents of the aryl is substituted with another aryl and may be referred to as diaryl. Each aryl of diaryl can be substituted as disclosed herein.

As used herein, "heteroaromatic" refers to an aromatic monocyclic system containing ring heteroatom selected from the group consisting of oxygen (O), nitrogen (N), sulfur (S), cerium (Si), and selenium (Se), or a polycyclic system with at least one ring which is aromatic and containing at least one ring heteroatom. Polycyclic heteroaryl contains one or more aromatic carbocyclic ring, non-aromatic carbocyclic ring and/or non-fused heteroaromatic rings. Heteroaryl may have, for example, aromatic ring containing 5 to 24 atoms, wherein the atoms including 1 to 5 hetero atoms (such as heteroaryl containing 5 to 20 members). Heteroaryl can be attached to a defined chemical structure at any heteroatom or carbon atom to form stable structure. Heteromatic ring usually does not contain linkages of O—O, S—S or S—O. However, one or more N or S atoms of the heteroaromatic may be oxidized (e.g., pyridine N-oxide, thiophene S-oxide, thiophene S, and S-dioxide). Examples of heteroaromatic includes monocyclic of 5 or 6 members and 5-6 bicyclic systems, wherein heteroaromatic may contain O, S, NH, N-alkyl, N-aryl, N-(arylalkane) (e.g., N-benzyl), $SiH_2$, Si(alkyl), Si(alkyl)$_2$, SiH(arylalkyl), Si(arylalkyl)$_2$, or Si(alkyl)(arylalkyl). Examples of such heteroaromatic rings include pyrrolyl, furyl, thienyl, pyridyl, pyrimidinyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, fluorenyl, isodecyl, benzofuranyl, benzothienyl, quinolinyl, 2-methylquinolyl, isoquinolyl, quinoxalyl, quinazolyl, benzotriazolyl, benzimidazolyl, benzothiazolyl, benzene isothiazolyl, benzisoxazole, benzoxazolyl, benzoxazolyl, cinnolinyl, 1H-carbazolyl, 2H-carbazolyl, indolizinyl, isobenzofuranyl, naphthyridinyl, phthalazinyl, pteridinyl, purinyl, oxazolopyridinyl, thiazolopyridyl, Imidazopyridyl, furopyridinyl, thienopyridyl, pyridopyrimidinyl, pyridopyrazinyl, pyridopyridazinyl, thienothiazolyl, thienooxazolyl, thienoimidazolyl, and the like. Further, examples of heteroaromatic include 4,5,6,7-tetrahydroindenyl, tetrahydroquinolyl, benzothienopyridinyl, benzofuropyridinyl, and the like. In some embodiments, heteroaryl can be substituted as disclosed herein.

Substituted cycloalkyl groups may, depending on the ring size, have one or more (e.g. 1, 2, 3, 4, 5 or more than 5) substituents. Preferably, each is independently selected from cycloalkyl, carbonylalkyl, aryl, heteroaryl, fluorine, chlorine, bromine, hydroxyl, mercapto, cyano, nitro, nitroso, formyl, acyl, carboxylate, alkylcarbonyloxy, carbamoyl, sulfonate, sulfamino, sulfamide, amidino.

In order to solve the problems in the prior art, the present invention provides a semiconductor mixed material for an active layer, which can effectively improve the electronic current leakage and increase the external quantum efficiency (EQE). Different from the semiconductor mixed material of the prior art comprises two electron donors and one electron acceptor, the semiconductor mixed material of the present invention based on one electron donor and two electron acceptors of the semiconductor mixed materials can provide better performance.

In one embodiment, the semiconductor mixed material of the present invention comprises an electron donor which is a conjugated polymer, a first electron acceptor with an energy gap less than 1.4 eV, and a second electron acceptor, wherein at least one of molecular stacking, π-π* stacking, and crystallinity of the second electron acceptor is less than that of the first electron acceptor. wherein, the electron donor is configured as a substrate for mixing the first electron acceptor and the second electron acceptor.

In this embodiment, the first electron acceptor comprises the following structure of Formula I:

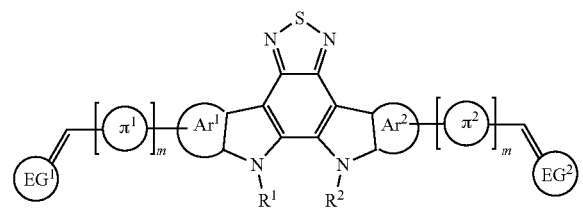

(Formula I)

wherein R1 and R2 can be the same or different, and $R^1$ and $R^2$ are independently selected from the group consisting of C1-C30 alkyl chain with substituents and without substitutents, and halogen; $Ar^1$, $Ar^2$, $EG^1$ and $EG^2$ can be the same or different, and $Ar^1$, $Ar^2$, $EG^1$ and $EG^2$ are independently selected from the group consisting of C1-C30 fused ring with and without substituents, C1-C30 fused heteroaromatic rings with and without substituents, and C1-C30 fused heterocyclic ring with and without substituents, benzene ring with and without substituents, five-membered heterocyclic ring with and without substituents, and six-membered heterocyclic ring with and without substituents; and π' and $π^2$ can be the same or different, and $π^1$ and $π^2$ are independently selected from the group consisting of C1-C30 fused ring with and without substituents, C1-C30 fused heterocyclic ring with and without substituents, C1-C30 fused ring with and without substituents, benzen ring with and without substituents, five-membered ring with and without substituents, and six-membered ring with and without substituents, alkene and alkyne with and without substituents, wherein m is an integer selected from 0 to 5;

In practice application, $R^1$ and $R^2$ can be the same or different, and $R^1$ and $R^2$ are independently selected from the group consisting of C1-C30 alkyl chain with carbon branched chain structure with substituents, and C1-C30 carbon branched chain structure without substituents.

In practice application, the substituents of the structure of Formula I are selected from the one of following groups: C1-C30 alkyl, C1-C30 branched alkyl, C1-C30 silyl, C1-C30 easter, C1-C30 alkoxy, C1-C30 alkylthio, C1-C30 haloalkyl, C1-C30 alkenyl, C1-C30 alkynyl, C1-C30 cyano-containing carbon chain, C1-C30 nitro-containing carbon chain, C1-C30 hydroxy-containing carbon chain, C1-C30 keto-containing carbon chain, oxygen, and halogen.
In practice application, the first electron acceptor can be selected from the following structures:
A1-1
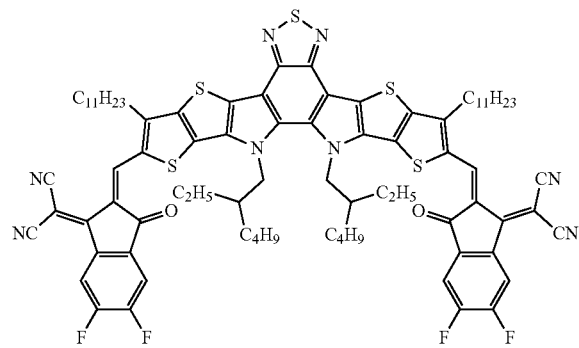
A1-2
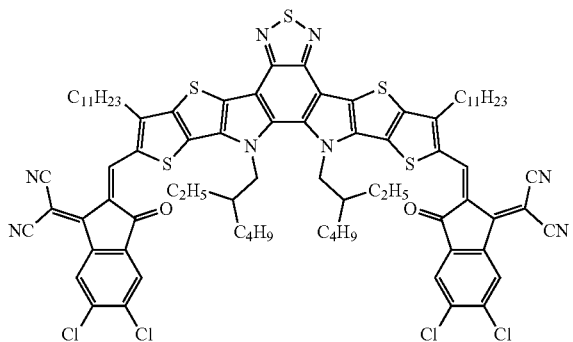
A1-3
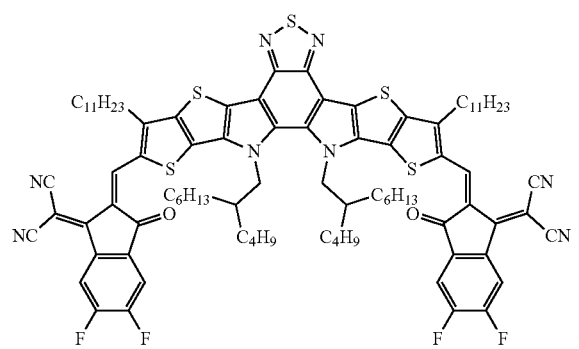
A1-4
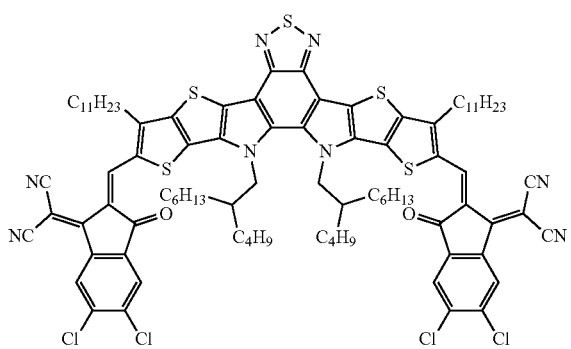
A1-5
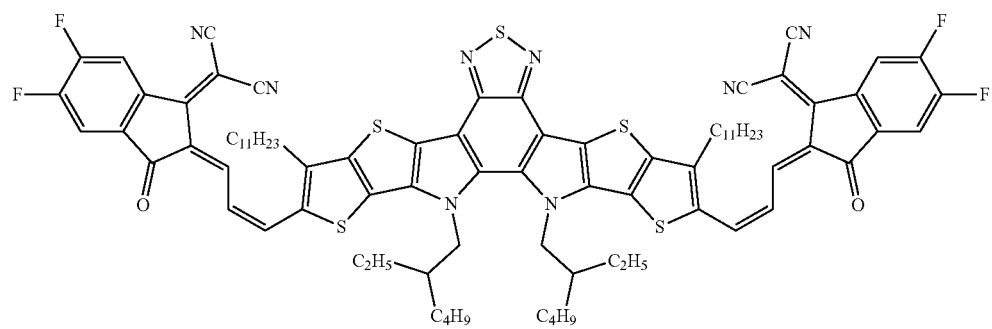
A1-6
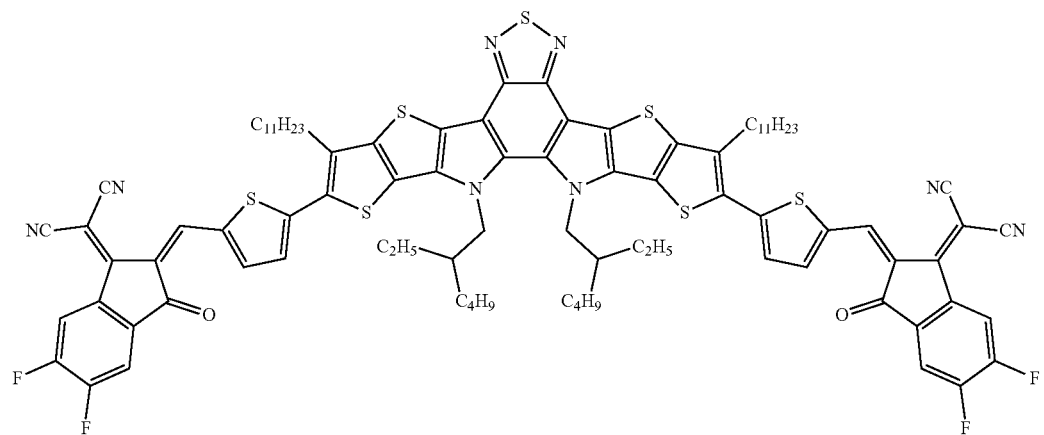

A1-7

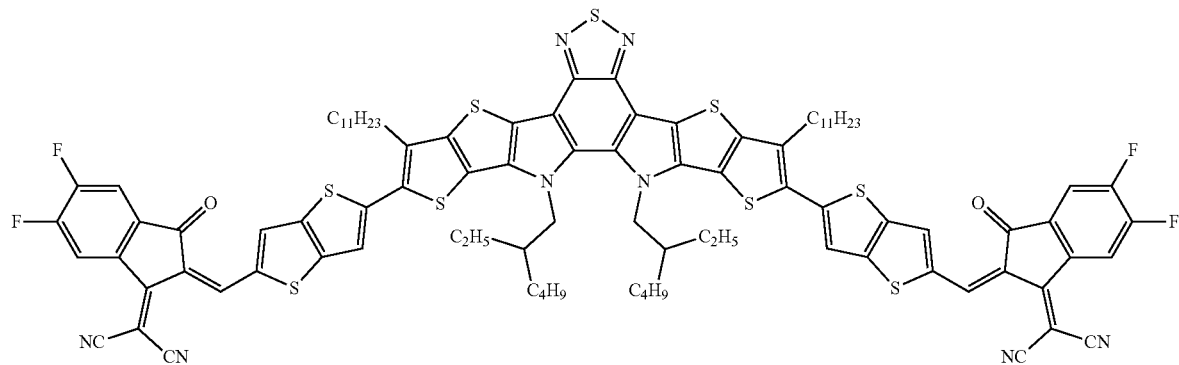

In this embodiment, the second electron acceptor comprises at least one structure of Formula II, Formula III, and Formula IV:

(Formula II)

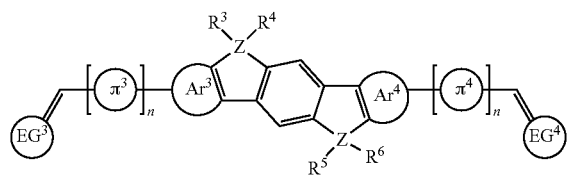

(Formula III)

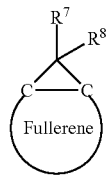

(Formula IV)

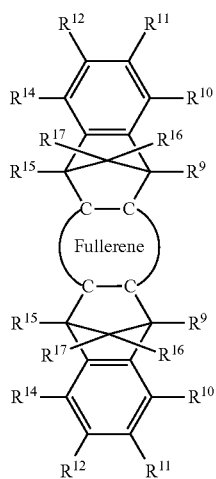

wherein, Z is selected from one of C, Si, and Ge; $R^3$ to $R^{17}$ can be the same or different, and $R^3$ to $R^{17}$ are independently selected from the group consisting of C1-C30 alkyl chain with substituents and without substituents and halogen; $Ar^3$, $Ar^4$, $EG^3$, $EG^4$ can be the same or different, and $Ar^3$, $Ar^4$, $EG^3$, $EG^4$ are independently selected from the group consisting of C1-C30 fused ring with and without substituents, C1-C30 fused heteroaromatic ring with and without substituents, and C1-C30 fused heterocyclic ring with and without substituents, benzene ring with and without substituents, five-membered heterocyclic ring with and without substituents, and six-membered heterocyclic ring with and without substituents; and $\pi^3$ and $\pi^4$ can be the same or different, and $\pi^3$ and $\pi^4$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents, alkene and alkyne with and without substituents, wherein m is an integer selected from 0 to 5.

In practice application, the substituents of the structure of Formula II, Formula III, and Formula IV are selected from the one of following groups: C1-C30 alkyl, C1-C30 branched alkyl, C1-C30 silyl, C1-C30 easter, C1-C30 alkoxy, C1-C30 alkylthio, C1-C30 haloalkyl, C1-C30 alkenyl groups, C1-C30 alkynyl groups, C1-C30 cyano-containing carbon chain, C1-C30 nitro-containing carbon chain, C1-C30 hydroxy-containing carbon chain, C1-C30 keto-containing carbon chain, oxygen, and halogen.

In practice application, the second electron acceptor can be selected from the following structures:

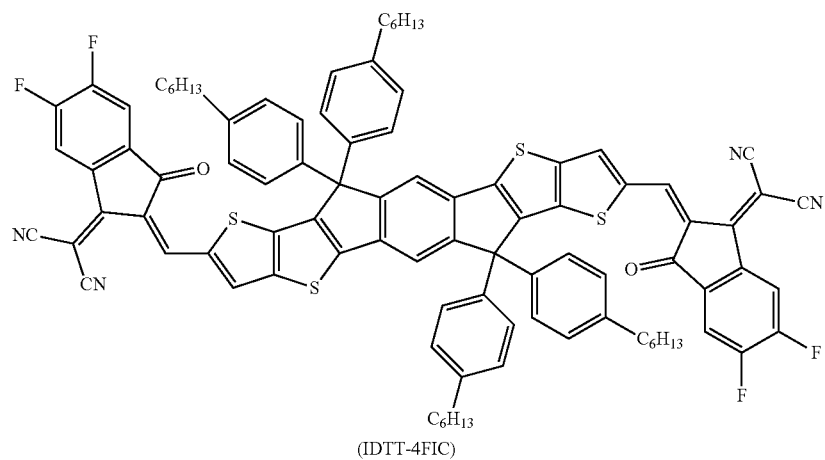
(IDTT-4FIC) A2-1
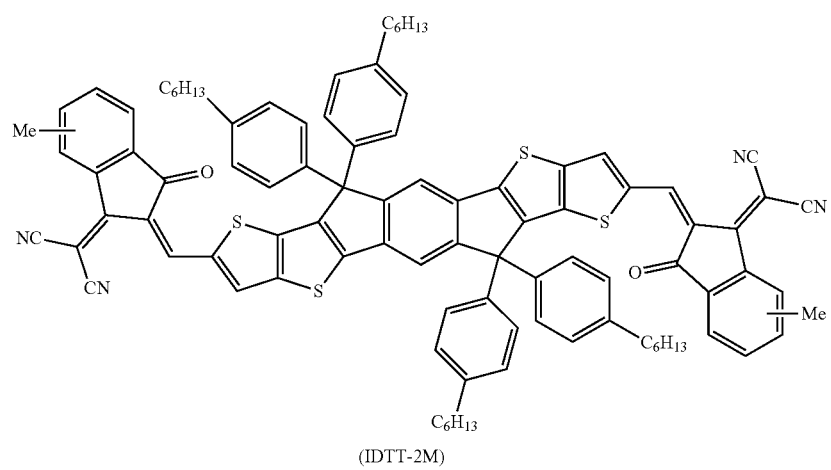
(IDTT-2M) A2-2
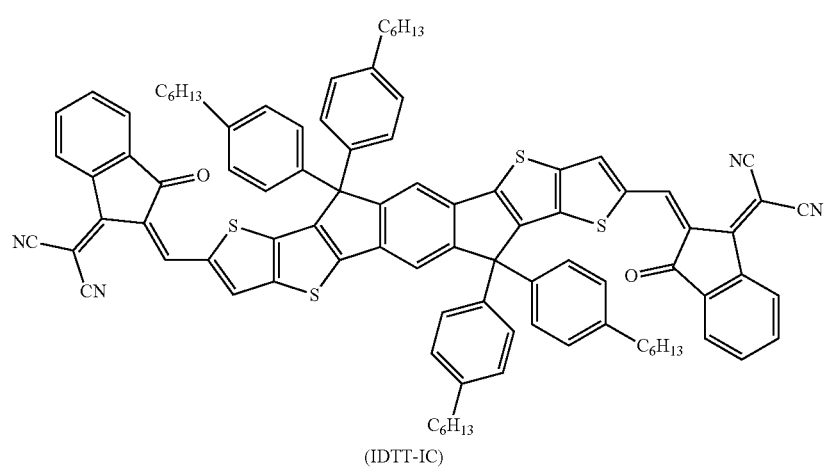
(IDTT-IC) A2-3

-continued
A2-4
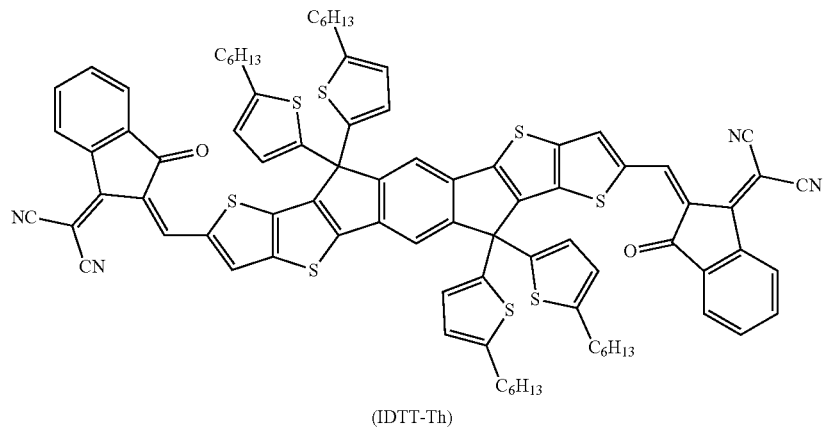
(IDTT-Th)
A2-5
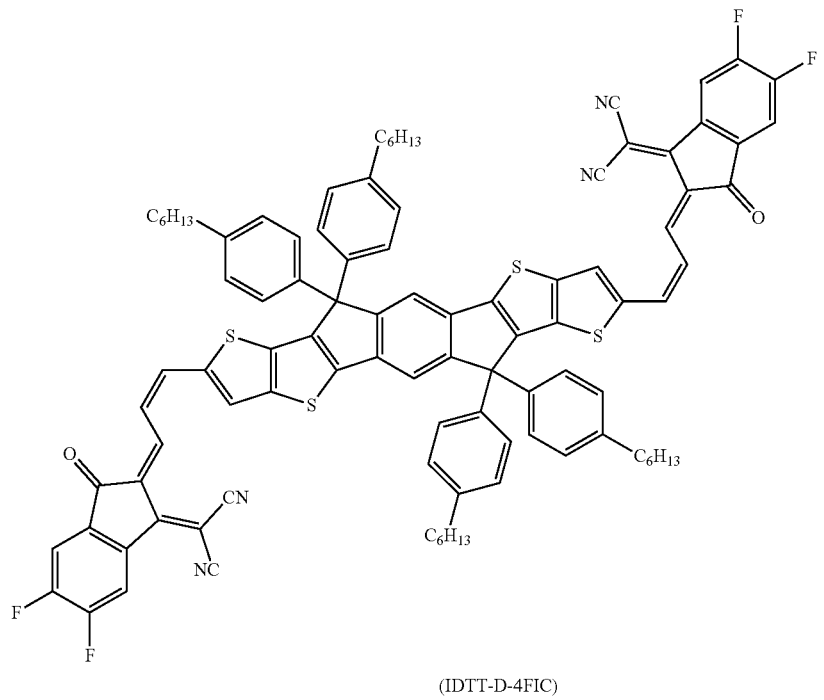
(IDTT-D-4FIC)
A2-6
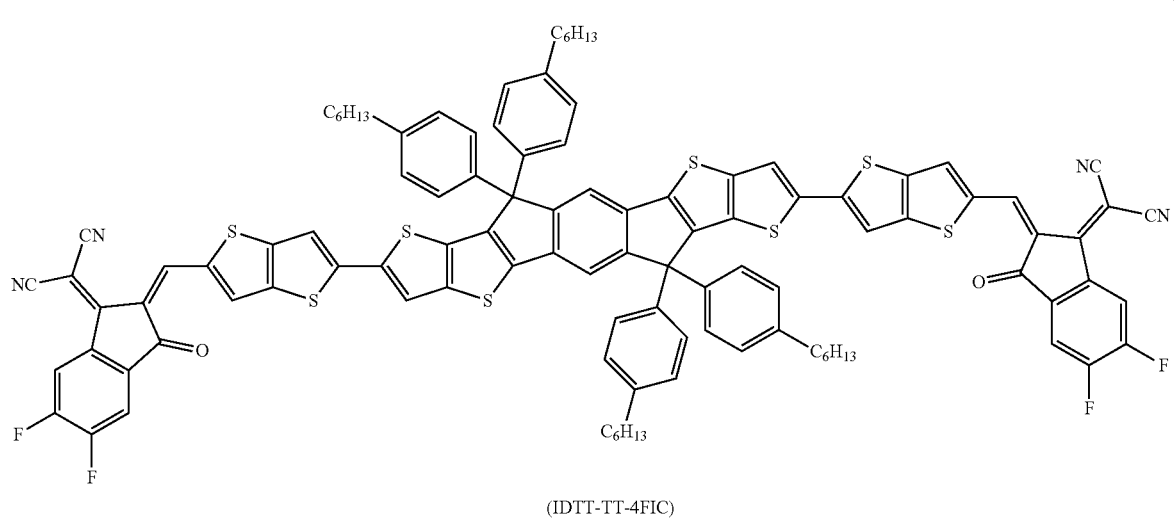
(IDTT-TT-4FIC)

-continued

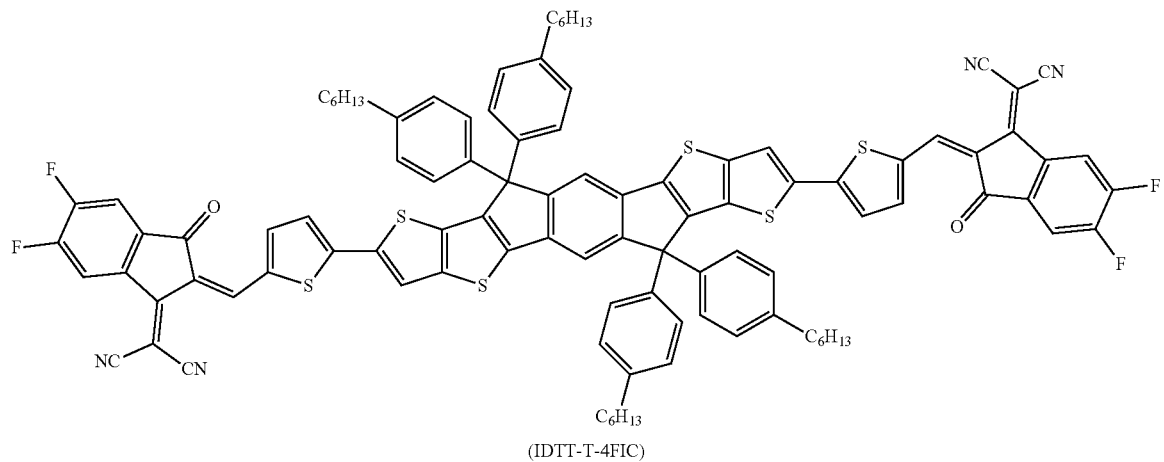
(IDTT-T-4FIC)

In this embodiment, the electron donor further comprises the following structure of Formula V:

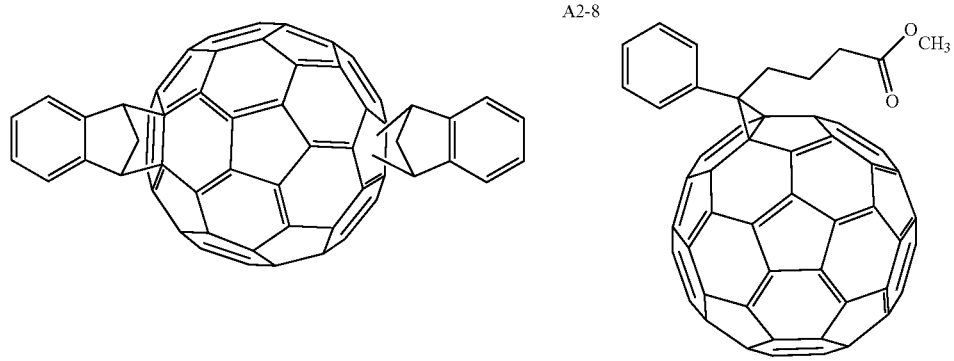
(Formula V)

wherein, X is selected from one of C, S, N, and O; $X_1$ to $X_4$ can be the same or different, and $X_1$ to $X_4$ are independently selected from the group consisting of C, C—F, C—Cl, C—Br, and C—I; $Ar^5$ to $Ar^8$ can be the same or different, and $Ar^5$ to $Ar^8$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered rings with and without substituents, and six-membered ring with and without substituents; $\pi^5$ and $\pi^6$ can be the same or different, and $\pi^5$ and $\pi^6$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, six-membered rins with and without substituents, and alkenes and alkynes with and without substituents; a to f can be the same or different, and a to f are integers independently selected from 0 to 5; and the sum of x and y is 1.

In practice application, one of $Ar^5$ to $Ar^8$ further comprises at least one of Si and S in the structure of Formula V.

In practice application, the substituents of the structure of Formula V are selected from the one of following groups: C1-C30 alkyl, C1-C30 branched alkyl, C1-C30 silyl, C1-C30 easter, C1-C30 alkoxy, C1-C30 alkylthio, C1-C30 haloalkyl, C1-C30 alkenyl, C1-C30 alkynyl, C1-C30 cyano-containing carbon chain, C1-C30 nitro-containing carbon chain, C1-C30 hydroxy-containing carbon chain, C1-C30 keto-containing carbon chain, oxygen, and halogen.

In practice application, the electron donors are selected from the following structures:

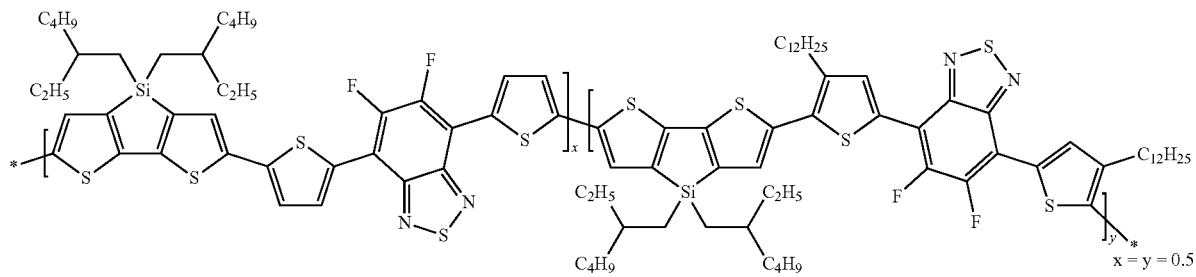
D-1
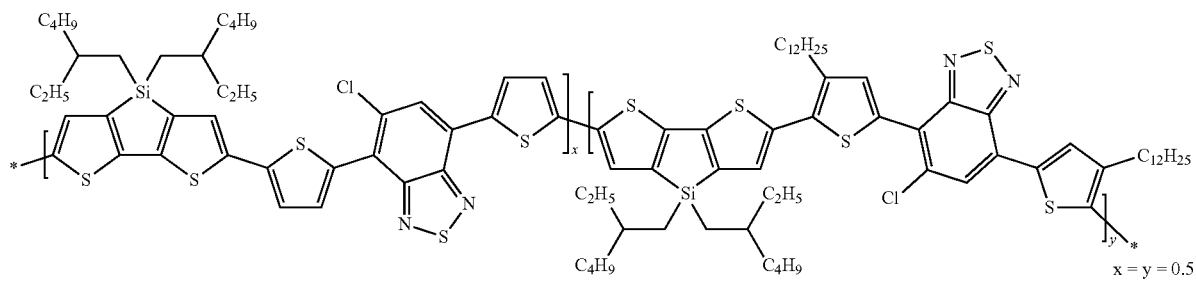
D-2
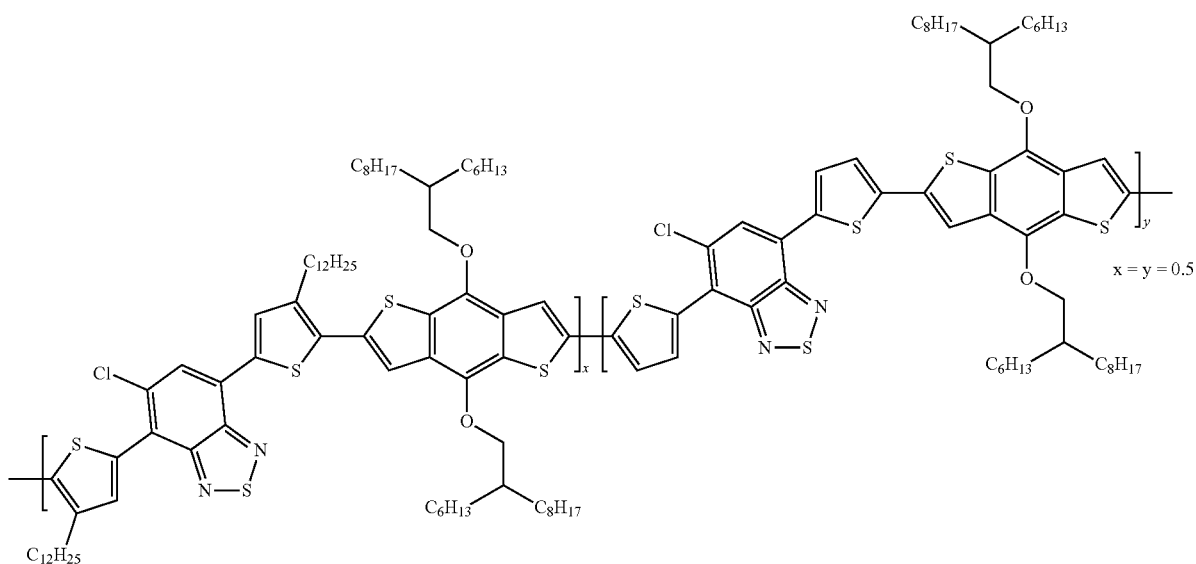
D-3
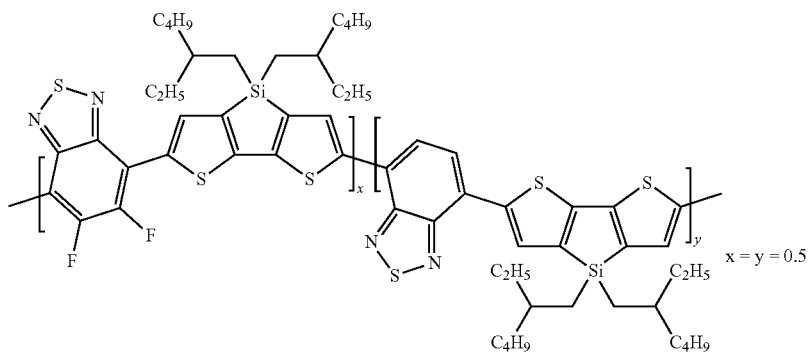
D-4

-continued

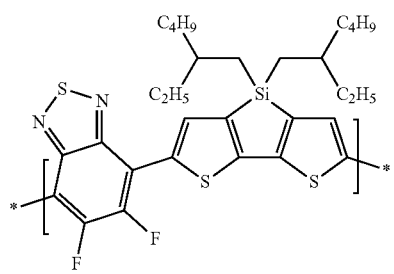

D-5

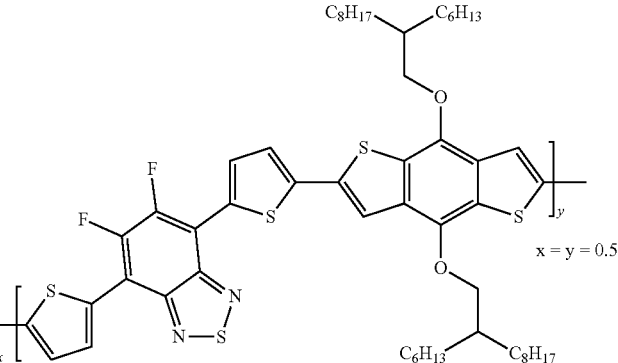

D-6

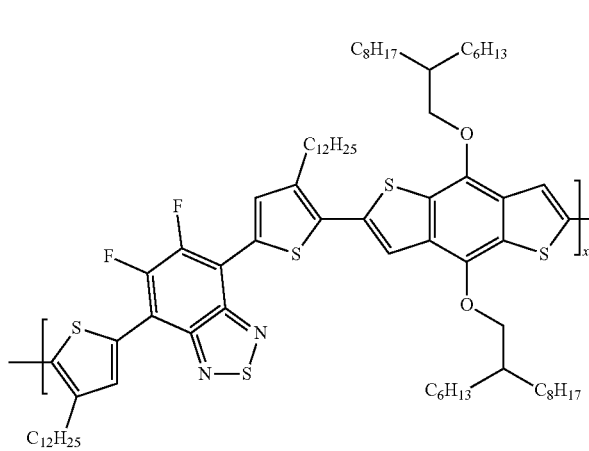

In this embodiment, solvent is selected from one or more of the following aromatic groups. In practice application, the boiling point of the solvent is between 80~250° C. The solvent can be selected from at least one of toluene, o-xylene, p-xylene, m-xylene, mesitylene, chlorobenzene, dichlorobenzene, trichlorobenzene, and tetrahydronaphthalene.

Please refer to FIG. 1. FIG. 1 shows a schematic structural diagram of one embodiment of the organic electronic device 1 of the present invention. As shown in FIG. 1. In another embodiment, the present invention further provides an organic electric device 1, which comprises a first electrode 11, a second electrode and an active layer. The active layer, which includes the aforementioned semiconductor mixed material, is disposed between the first electrode and the second electrode. In practice application, the organic electric device may have a laminated structure, which sequentially includes a substrate 10, the first electrode 11 (transparent electrode), an electron transfer layer (ETL) 12, the active layer 13, a hole transfer layer (HTL) 14 and the second electrode 15. In addition, the organic electric device 1 may include an organic photovoltaic device, an organic light sensing device, an organic light emitting diode, and an organic thin film transistor (OTFT)

Preparation of the Active Layer:

In order to make a suitable ratio of the semiconductor mixed material as the active layer material, preparing three different kinds of the weight percentage ratio of the semiconductor mixed materials, and the ratio of that are the electron donor (abbreviation D): the first electron acceptor (abbreviation A1): the second electron acceptor (abbreviation A2)=1:1.2:0, 1:1:0.2, and 1:0.8:0.4.

Preparation and Measurement of the Organic Electron Device:

A glass coated by a pre-patterned Indium Tin Oxides (ITO) with a sheet resistance of ~15 Ω/sq is used as a substrate. The substrate is ultrasonically oscillated in soap deionized water, deionized water, acetone, and isopropanol in sequence, and washed in each step for 15 minutes. The washed substrate is further treated with a UV-ozone cleaner for 30 minutes. A top coating layer of ZnO (diethylzinc solution, 15 wt % in toluene, diluted with tetrahydrofuran) is spin coated on the ITO substrate with a rotation rate of 5000 rpm for 30 seconds, and then baked at 150° C. in air for 20 minutes. The active layer solution was prepared in o-xylene. The active layer includes the aforementioned organic semiconductor material. To completely dissolve the active layer material, the active layer solution is stirred on a hot plate at 120° C. for at least 1 hour. Then, the active layer material is returned to the room temperature for spin coating. Finally, the thin film formed by the coated active layer is annealed at 120° C. for 5 minutes, and then transferred to a thermal evaporation machine. A thin layer (8 nm) of MoO3 is deposited as an anode intermediate layer under a vacuum of 3×10-6 Torr, and then a silver layer with a thickness of 100 nm is deposited as an upper electrode. All batteries are encapsulated with epoxy resin in the glove box to make organic electronic components (ITO/ETL/active layer/MoO3/Ag). The J-V characteristics of the components is measured by a solar simulator (having a xenon lamp with an AM 1.5G filter) in air and at room temperature and under AM 1.5 G (100 mW cm-2). Herein, a standard ruthenium dipole with a KG5 filter is used as a reference cell to calibrate the light intensity to make the mismatch portion of the spectrum consistent. The J-V characteristics are recorded by a Keithley 2400 source meter instrument. A typical battery has an element area of 4 mm2, which is defined by the area of the metal mask aligning element with the aperture.

Figure 2:
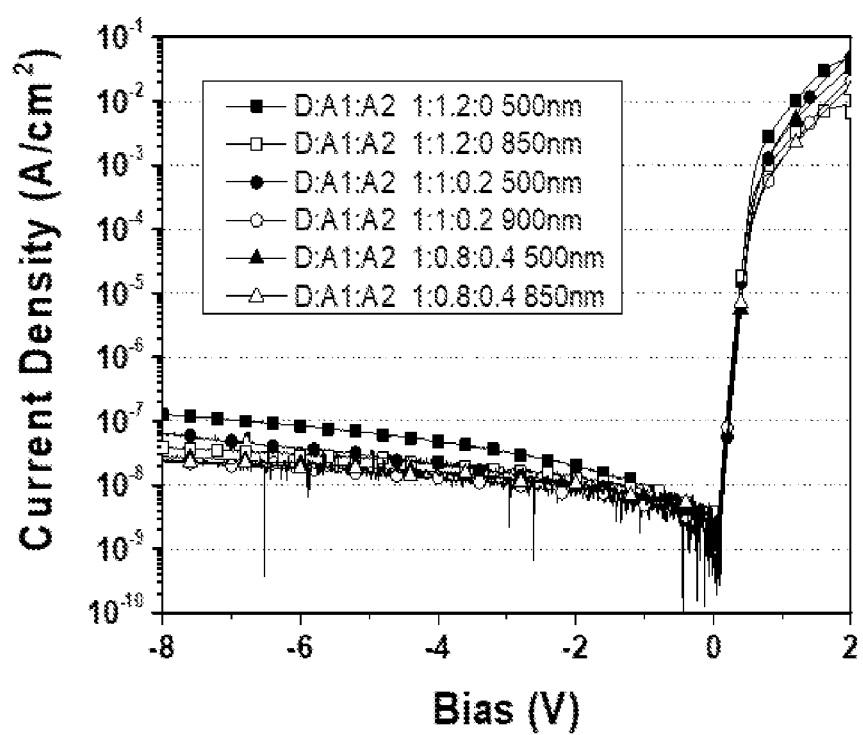
FIG. 2 shows the test results of the current density of the organic electronic device with three different ratios of the semiconductor mixed materials of the present invention as the active layer material under two different thicknesses of the active layer materials.
Figure 3:
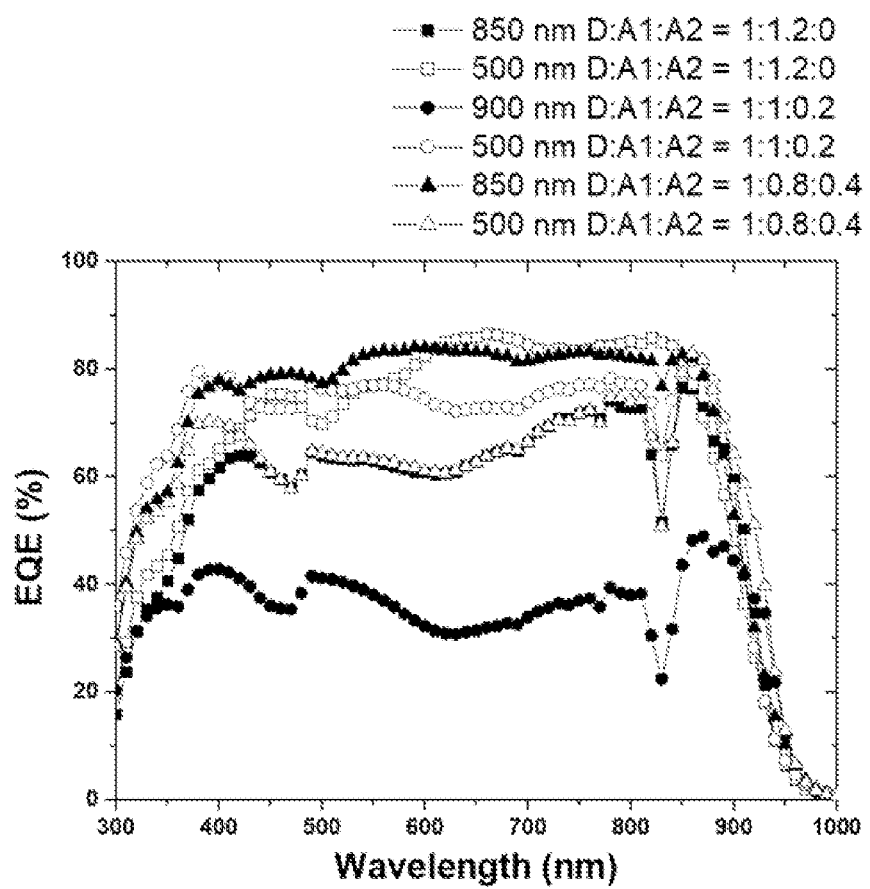
FIG. 3 shows the test results of external quantum efficiency (EQE) of the organic electronic device with three different ratios of the semiconductor mixed materials of the present invention as the active layer material under two different thicknesses of the active layer materials.
Figure 4:
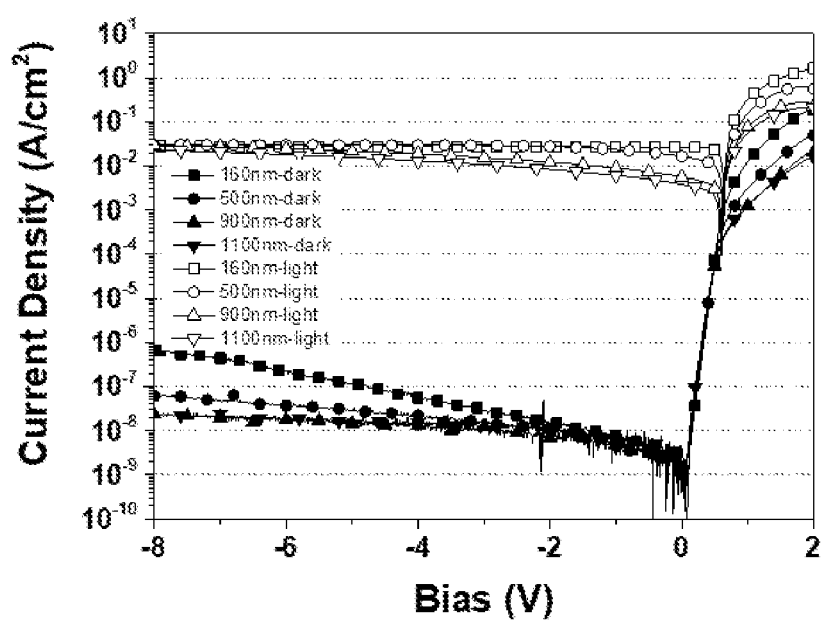
FIG. 4 shows the test results of the electronic current density of the organic electronic device with different thicknesses of the semiconductor mixed materials of the present invention as the active layer material.
Figure 5:
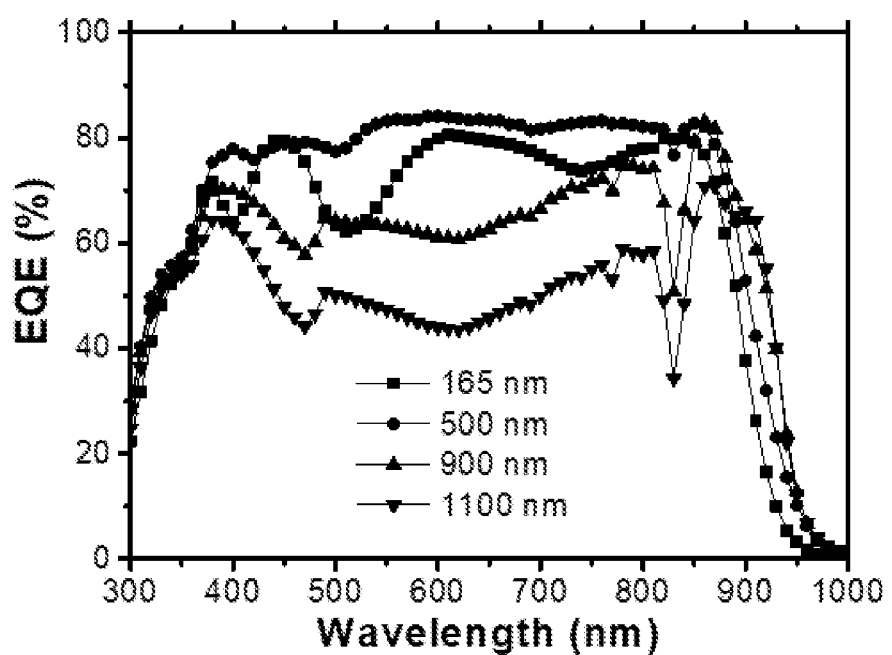
FIG. 5 shows the test results of external quantum efficiency (EQE) of the organic electronic device with different thicknesses of the semiconductor mixed materials of the present invention as the active layer material.

The Performance Analysis of Organic Electronic Device: Please refer to Table 1, FIG. 2. and FIG. 3, Table 1 shows the performance test results of the organic electronic devices with three different ratios of the semiconductor mixed materials of the present invention as the active layer material under two different thicknesses of the active layer materials. FIG. 2 shows the test results of the current density of the organic electronic device with three different ratios of the semiconductor mixed materials of the present invention as the active layer material under two different thicknesses of the active layer materials. FIG. 3 shows the test results of external quantum efficiency (EQE) of the organic electronic device with three different ratios of the semiconductor mixed materials of the present invention as the active layer material under two different thicknesses of the active layer materials.

with different thicknesses of the semiconductor mixed materials of the present invention as the active layer material under two different thicknesses of the active layer materials. FIG. 4 shows the test results of the electronic current density of the organic electronic device with different thicknesses of the semiconductor mixed materials of the present invention as the active layer material. FIG. 5 shows the test results of external quantum efficiency (EQE) of the organic electronic device with different thicknesses of the semiconductor mixed materials of the present invention as the active layer material.

TABLE 2

| Thickness of the active layer material (nm) | $V_{oc}$ (V) | $J_{sc}$ (mA/cm$^2$) | FF (%) | PCE (%) | $I_D$@ −8 V (A/cm$^2$) | $I_{ph}$ @ −8 V (mA/cm$^2$) |
|---|---|---|---|---|---|---|
| 165 | 0.67 | 25.2 | 70.7 | 11.93 | $7.4 \times 10^{-7}$ | 27.9 |
| 500 | 0.65 | 17.5 | 49.9 | 6.48 | $6.1 \times 10^{-8}$ | 29.9 |
| 900 | 0.61 | 6.6 | 49.5 | 1.98 | $2.3 \times 10^{-8}$ | 28.9 |
| 1100 | 0.59 | 4.1 | 49.8 | 1.30 | $2.2 \times 10^{-8}$ | 23.0 |

As shown in Table 2, FIG. 4 and FIG. 5, prepare the active layer materials of the organic electronic device with the ratio

TABLE 1

| D:A$_1$:A$_2$ | Thickness of the active layer (nm) | $V_{oc}$ (V) | $J_{sc}$ (mA/cm$^2$) | FF (%) | PCE (%) | $I_D$@ −8 V (A/cm$^2$) | $I_{ph}$ @ −8 V (mA/cm$^2$) |
|---|---|---|---|---|---|---|---|
| 1:1.2:0 | ~500 | 0.61 | 13.3 | 48.7 | 3.95 | $1.3 \times 10^{-7}$ | 32.6 |
|  | ~850 | 0.58 | 5.60 | 49.5 | 1.60 | $3.8 \times 10^{-7}$ | 31.1 |
| 1:1:0.2 | ~500 | 0.64 | 17.5 | 50.0 | 5.60 | $6.1 \times 10^{-8}$ | 29.9 |
|  | ~900 | 0.61 | 6.60 | 49.5 | 1.98 | $2.3 \times 10^{-8}$ | 28.9 |
| 1:0.8:0.4 | ~500 | 0.66 | 22.3 | 48.0 | 7.08 | $2.8 \times 10^{-8}$ | 32.9 |
|  | ~850 | 0.63 | 8.70 | 46.0 | 2.53 | $2.5 \times 10^{-8}$ | 32.8 |

In the semiconductor mixed materials, the electron donor can be used as substrate, the first electron acceptor can be used as a dye pigment to absorb red light and near-infrared light, and the second electron acceptor can be used as an additive to adjust the morphology of the active layer. As shown in Table 1 and FIG. 2, the leakage current is reduced when the addition amount of the second electron acceptor increases. As shown in FIG. 3, the external quantum efficiency of thickness of the active layer material which is 500 nm is higher than the external quantum efficiency of thickness of the active layer material is over 850 nm, which shows that different thicknesses of the active layer materials will affect the external quantum efficiency. Moreover, the external quantum efficiency can be significantly improved when the addition amount of the second electron acceptor is increased. Furthermore, it was found that adding the fullerene can induce the spectrum become a blue shift of the organic electronic device during the experiment. In the wavelength range of 850 nm to 900 nm in FIG. 3, the more fullerenes, the blue shift will be more obvious of the test results. As can be seen from the above test results, the organic electronic devices which prepared with the ratio of the electron donor (D): the first electron acceptor (A1): the second electron acceptor (A2)=1:0.8:0.4 have better external quantum efficiency and lower leakage current, so the next step is to test the thickness of the semiconductor mixed material with this ratio.

Please refer to Table 2, FIG. 4. and FIG. 5. Table 2 shows the performance test results of the organic electronic device of the electron donor (D): the first electron acceptor (A1): the second electron acceptor (A2)=1:0.8:0.4 with thickness as 165 nm, 500 nm, 900 mn and 1100 nm, respectively. It has better leakage suppression capability for leakage current when the thickness of the active layer material is greater than 500 nm. As the thickness of the active layer material increases, the spectrum of the organic electronic device will be red shift. This can be attributed to the increase in molecular stackability, π-π* stackability and crystallinity when the thickness of the active layer material increases. Therefore, the photocurrent and external quantum efficiency (EQE) also vary as the thickness of the active layer.

Figure 6A:
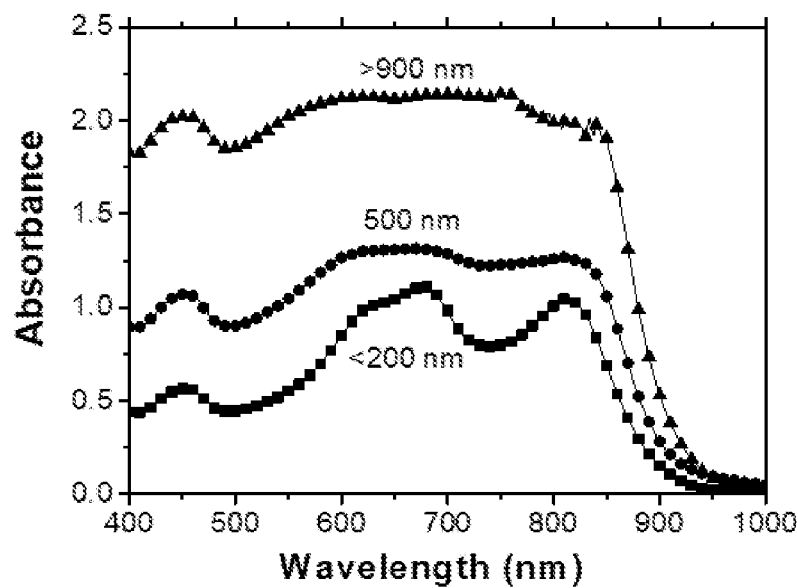
FIG. 6A shows the absorbance test results of the organic electronic device with different thicknesses of the semiconductor mixed materials of the present invention as the active layer material.
Figure 6B:
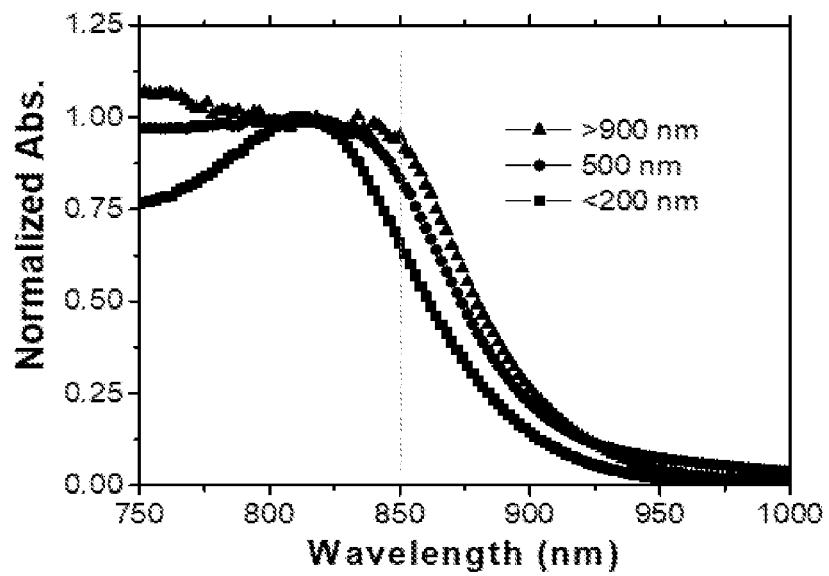
FIG. 6B is according to the absorbance test results in FIG. 6A of the normalized data between the 750 nm-1000 nm.
Figure 7A:
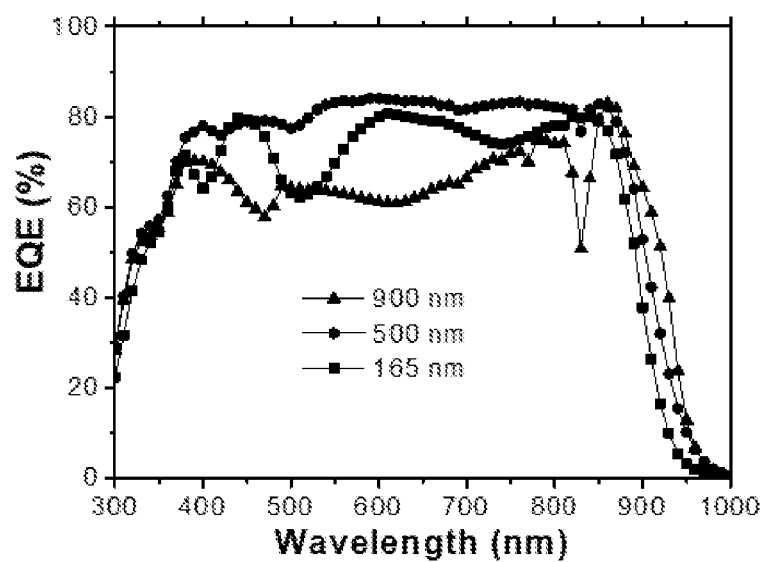
FIG. 7A shows the test results of external quantum efficiency (EQE) of the organic electronic device with different thicknesses of the semiconductor mixed materials of the present invention as the active layer material.
Figure 7B:
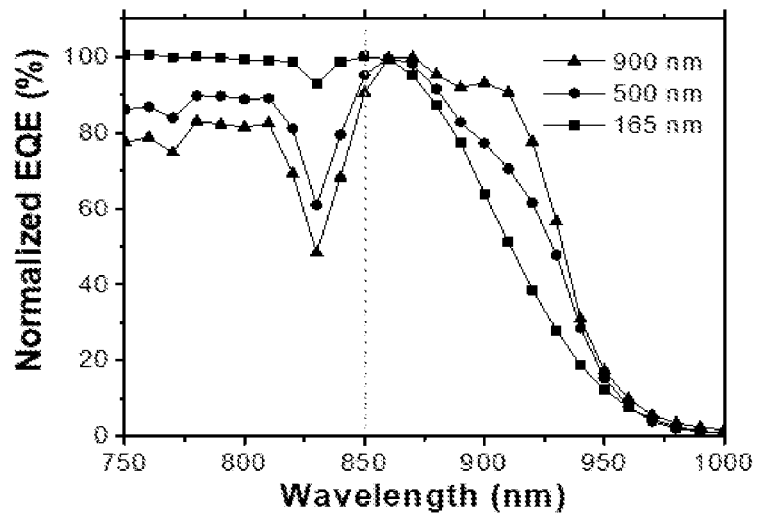
FIG. 7B is according to the absorbance test results in FIG. 7A of the external quantum efficiency (EDE) of the normalized data between the 750 nm-1000 nm.

Please refer to FIG. 6A to FIG. 7B. FIG. 6A shows the absorbance test results of the organic electronic device with different thicknesses of the semiconductor mixed materials of the present invention as the active layer material. FIG. 6B is according to the absorbance test results in FIG. 6A of the normalized data between the 750 nm~1000 nm. FIG. 7A shows the test results of external quantum efficiency (EQE) of the organic electronic device with different thicknesses of the semiconductor mixed materials of the present invention as the active layer material. FIG. 7B is according to the absorbance test results in FIG. 7A of the external quantum efficiency (EDE) of the normalized data between the 750 nm~1000 nm. As shown in FIG. 6A to FIG. 7B, as the thickness of the active layer material increases, the spectrum of the organic electronic device will be red shift. This can be attributed to the increase in the molecular stackability, π-π* stackability and crystallinity when the thickness of the active layer material increases. The increase in the molecular stackability, π-π* stackability, and crystallinity can be attributed to the longer drying time during the thick film formation process which makes the molecular stackability and π-π* stackability and crystallinity of the first electron acceptor to be improved.

Figure 8:
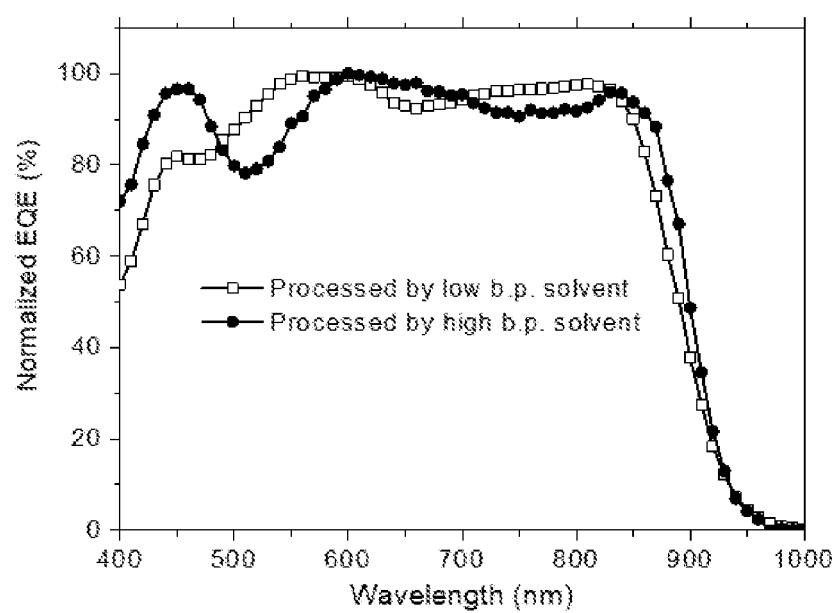
FIG. 8 shows the test results of external quantum efficiency (EQE) of the organic electronic device with different processing solvents of the semiconductor mixed materials of the present invention.

Please refer to FIG. 8, FIG. 8 shows the test result of external quantum efficiency (EQE) of the organic electronic device with different processing solvents of the semiconductor mixed materials of the present invention. As shown in FIG. 8, wherein the high point solvent: o-xylene (boiling point is 146° C. at 760 mm-Hg) and the low boiling point solvent: chloroform (boiling point is 61° C. at 760 mm-Hg) are used as the processing solvent for experiments. It can be found that organic electronic device prepared with the high boiling point solvent: o-xylene shows red shift in spectrum. It can be seen that the spectrum of the high boiling point solvent will affect the shift, and the main reason for the shift of the spectrum is the change of molecular stacking, π-π* stacking and crystallinity. The higher boiling point of the solvent, the longer time for drying and the longer time for molecular stacking, so as to the molecular stackability, π-π** stackability and crystallinity will increase; on the contrary, speeding up the drying time shortens the time for molecular stacking and arrangement when the boiling point of the solvent is lower so as to molecular stackability, π-π* stackability and crystallinity will be reduced.

Compared with the prior art, the semiconductor mixed material of the present invention can effectively improve the leakage current of organic electronic device, external quantum efficiency (EQE) and improves the spectrum of the near-infrared light region greater than 800 nm. In addition, environmentally friendly solvent treatment can be used in mass production and manufacturing.

With the detailed description of the above embodiments, it is hoped that the features and spirit of the present invention can be more clearly described, and the scoped of the present invention is not limited by the embodiments disclosed above. On the contrary, the intention is to cover various changes and equivalent arrangements within the scope of the patents to be applied for in the present invention.

What is claimed is:

1. A semiconductor mixed material, comprising:
an electron donor which is a random copolymer with at least two structural units randomly arranged comprising the structure of Formula V:

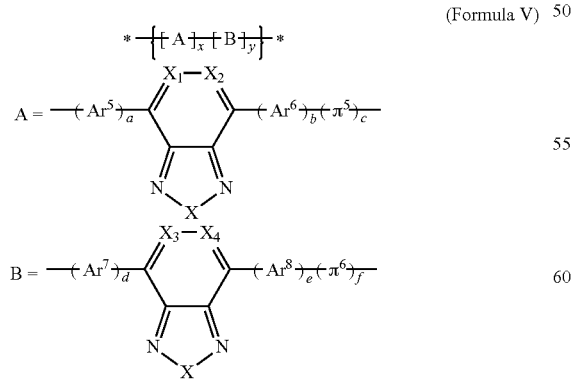

(Formula V)

wherein, the structural units comprise A and B, the electron donor comprises continuous a plurality of monomers with Formula V, and the number of A and B of each monomer with Formula V is random, and an arrangement with A and B of each monomer is random, without an arrangement with only a single A and a single B of each monomer;

X is selected from one of following: C, S, N, and O;

$X_1$ to $X_4$ can be the same or different, and $X_1$ to $X_4$ are independently selected from the group consisting of C, C—F, C—Cl, C—Br, and C—I;

$Ar^5$ to $Ar^8$ an be the same or different, and $Ar^5$ to $Ar^8$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents, wherein Formula V comprises at least one of $Ar^5 \neq Ar^5 \neq$ and $Ar^7 \neq Ar^8$;

$\pi^5$ and $\pi^6$ can be the same or different, and $\pi^5$ and $\pi^6$ are independently selected from the group consisting of C8-C30 fused ring with and without substituents, C8-C30 fused heteroaromatic ring with and without substituents, C8-C30 fused heterocyclic ring with and without substituents, wherein $Ar^5$ to $Ar^8$ are different from $\pi^5$ and $\pi^6$;

a to f can be the same or different, and a to f are integers independently selected from 1 to 5; and the sum of x and y is 1, $x \neq 0$ and $y \neq 0$;

a first electron acceptor with an energy gap less than 1.4 eV, the first electron acceptor comprising a structure of Formula 1:

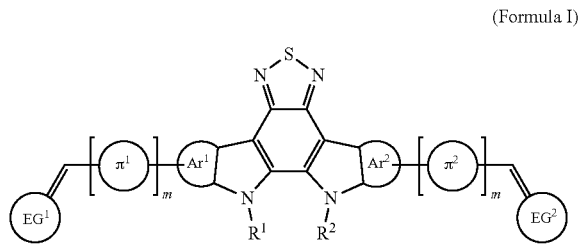

(Formula I)

wherein $R^1$ and $R^2$ can be the same or different, and $R^1$ and $R^2$ are independently selected from the group consisting of C1-C30 alkyl chain with and without substitutents, and halogen;

$Ar^1$, $Ar^2$, $EG^1$ and $EG^2$ can be the same or different, and $Ar^1$, $Ar^2$, $EG^1$ and $EG^2$ are independently selected from the group consisting of C1-C30 fused ring with and without substituents, C1-C30 fused heteroaromatic ring with and without substituents, and C1-C30 fused heterocyclic ring with and without substituents, benzene ring with and without substituents, five-membered heterocyclic ring with and without substituents, and six-membered heterocyclic ring with and without substituents; and $\pi^1$ and $\pi^2$ can be the same as or different from each other, and $\pi^1$ and $\pi^2$ are independently selected from the group consisting of C1-C30 fused rings with and without substituents, C1-C30 fused heterocyclic ring with and without substituents, C1-C30 fused ring with and without substituents, benzene ring with and without substituents, five-membered ring with and without substituents, and six-membered ring with and without substituents, alkene with and without substituents and alkyne with and without substituents, wherein m is an integer selected from 0 to 5; and a second electron acceptor, wherein at least one of molecular stack ability, π-π* stack ability, and crystallinity of the second electron acceptor is less than that of the first electron acceptor;

wherein, the electron donor is configured as a substrate for mixing the first electron acceptor and the second electron acceptor.

2. The semiconductor mixed material of claim 1, wherein $R^1$ and $R^2$ can be the same or different, and $R^1$ and $R^2$ are respectively selected from the group consisting of C1-C30 alkyl chain with carbon branched chain structure with substituents and without substituents.

3. The semiconductor mixed material of claim 1, wherein the substituent of Formula I is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 alkenyl, C1-C30 alkynyl, C1-C30 cyano-containing carbon chain, C1-C30 nitro-containing carbon chain, C1-C30 hydroxy-containing carbon chain, C1-C30 keto-containing carbon chain, oxygen, and halogen.

4. The semiconductor mixed material of claim 1, wherein the second acceptor comprises at least one structure of Formula II, Formula III, and Formula IV:

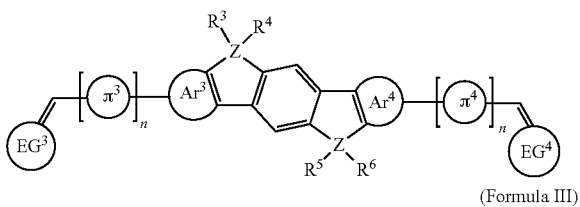
(Formula II)

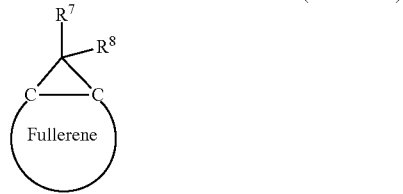
(Formula III)

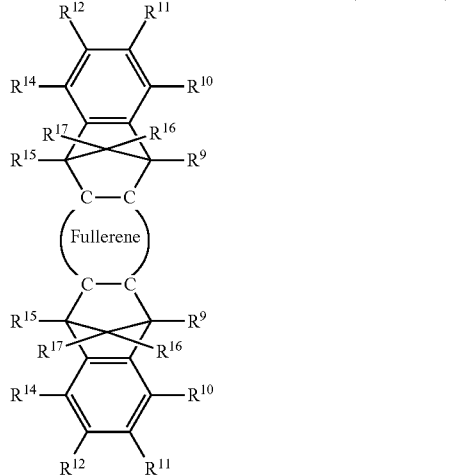
(Formula IV)

wherein, Z is selected from one of following: C, Si, and Ge;

$R^3$ to $R^{17}$ can be the same or different, and $R^3$, $AR^{17}$ are independently selected from the group consisting of C1-C30 alkyl chain with and without substituents and halogen;

$Ar^3$, $Ar^4$, $EG^3$, $EG^4$ can be the same or different, and $Ar^3$, $Ar^4$, $EG^3$, $EG^4$ are independently selected from the group consisting of C1-C30 fused ring with and without substituents, C1-C30 fused heteroaromatic ring with and without substituents, and C1-C30 fused heterocyclic ring with and without substituents, benzene ring with and without substituents, five-membered heterocyclic ring with and without substituents, and six-membered heterocyclic ring with and without substituents; and $\pi^3$ and $\pi^4$ can be the same or different, and $\pi^3$ and $\pi^4$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents, alkene and alkyne with and without substituents, wherein m is an integer selected from 0 to 5.

5. The semiconductor mixed material of claim 1, wherein one of $Ar^5$ to $Ar^8$ further comprises at least one of Si and S.

6. The semiconductor mixed material of claim 1, wherein the weight percentage of the first electron acceptor is not less than that of the second electron acceptor in the semiconductor mixed material.

7. A semiconductor mixed material, comprising:
an electron donor which is a random copolymer with at least two structural units randomly arranged comprising the structure of Formula V:

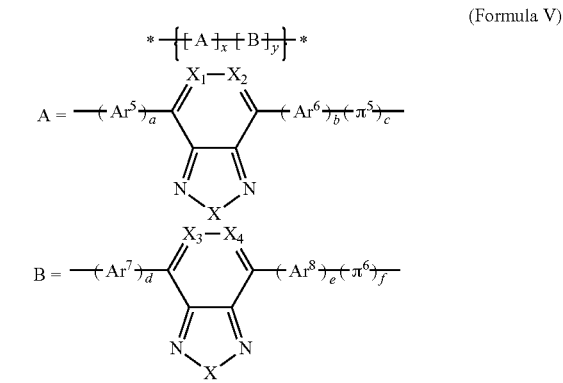
(Formula V)

wherein, the structural units comprise A and B, the electron donor comprises continuous a plurality of monomers with Formula V, and the number of A and B of each monomer with Formula V is random, and an arrangement with A and B of each monomer is random, without an arrangement with only a single A and a single B of each monomer;

X is selected from one of following: C, S, N, and O;

$X_1$ to $X_4$ can be the same or different, and $X_1$ to $X_4$ are independently selected from the group consisting of C, C—F, C—Br, and C—I;

$Ar^5$ to $Ar^8$ can be the same or different, and $Ar^5$ to $Ar^8$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents, wherein Formula V comprises at least one of $Ar^5 \neq Ar^7$ and $Ar^6 \neq Ar^8$;

$\pi^5$ and $\pi^6$ can be the same or different, and $\pi^5$ and $\pi^6$ are independently selected from the group consisting of C8-C30 fused ring with and without substituents, C8-C30 fused heteroaromatic ring with and without substituents, C8-C30 fused heterocyclic ring with and without substituents, wherein $Ar^5$ to $Ar^8$ are different from $\pi^5$ and $\pi^6$;

a to f can be the same or different, and a to f are integers independently selected from 1 to 5; and the sum of x and y is 1, $x \neq 0$ and $y \neq 0$;

a first electron acceptor with an energy gap less than 1.4 eV;

a second electron acceptor, at least one of molecular stack ability, π-π* stack ability, crystallinity of the second electron acceptor less than that of the first electron acceptor, and the second electron acceptor comprising at least one of the structure of Formula II, Formula III, and Formula IV:

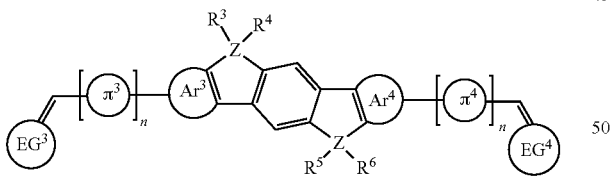

(Formula II)

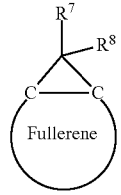

(Formula III)

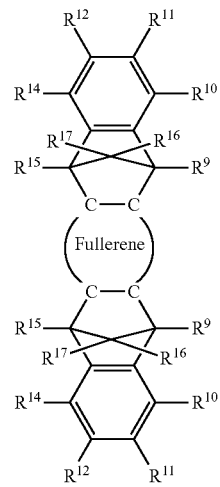

(Formula IV)

wherein, Z is selected from one of following: C, Si, and Ge;

$R^3$ to $R^{17}$ can be the same or different, and $R^3$ to $R^{17}$ are independently selected from the group consisting of C1-C30 alkyl with substituents and without substituents and halogen;

$Ar^3$, $Ar^4$, $EG^3$, $EG^4$ can be the same or different, and $Ar^3$, $Ar^4$, $EG^3$, $EG^4$ are independently selected from the group consisting of C1-C30 fused ring with and without substituents, C1-C30 fused heteroaromatic ring with and without substituents, and C1-C30 fused heterocyclic ring with and without substituents, benzene ring with and without substituents, five-membered ring with and without substituents, and six-membered ring with and without substituents; and $\pi^3$ and $\pi^4$ can be the same or different, and $\pi^3$ and $\pi^4$ are independently selected from the group consisting of C1-C30 fused ring with and without substituents, C1-C30 fused heteroaromatic ring with and without substituents, C1-C30 fused heterocyclic ring with and without substituents, benzene ring with and without substituents, five-membered ring with and without substituents, and six-membered ring with and without substituents, alkene with and without substituents and alkyne with and without substituents, wherein m is an integer selected from 0 to 5;

wherein, the electron donor is configured as a substrate for mixing the first electron acceptor and the second electron acceptor.

8. An organic electronic device, comprising:

a first electrode;

a second electrode; and an active layer material, which is located between the first electrode and the second electrode, wherein the active layer material comprises the semiconductor mixed material as described in any one of claim 1 and claim 7.

* * * * *